(12) United States Patent
Hughett et al.

(10) Patent No.: US 11,944,740 B2
(45) Date of Patent: Apr. 2, 2024

(54) FLUID COLLECTION DEVICES, RELATED SYSTEMS, AND RELATED METHODS

(71) Applicant: PUREWICK CORPORATION, El Cajon, CA (US)

(72) Inventors: James David Hughett, Monroe, GA (US); Eric Rehm, Lawrenceville, GA (US)

(73) Assignee: PUREWICK CORPORATION, Covington, GA (US)

( * ) Notice: Subject to any disclaimer, the term of this patent is extended or adjusted under 35 U.S.C. 154(b) by 330 days.

(21) Appl. No.: 17/051,550

(22) PCT Filed: Apr. 29, 2019

(86) PCT No.: PCT/US2019/029609
§ 371 (c)(1),
(2) Date: Oct. 29, 2020

(87) PCT Pub. No.: WO2019/212950
PCT Pub. Date: Nov. 7, 2019

(65) Prior Publication Data
US 2021/0228795 A1    Jul. 29, 2021

Related U.S. Application Data

(60) Provisional application No. 62/665,331, filed on May 1, 2018.

(51) Int. Cl.
*A61F 5/44* (2006.01)
*A61F 5/455* (2006.01)
*A61M 1/00* (2006.01)

(52) U.S. Cl.
CPC ............ *A61M 1/80* (2021.05); *A61F 5/4401* (2013.01); *A61F 5/4408* (2013.01); *A61F 5/455* (2013.01);
(Continued)

(58) Field of Classification Search
CPC .......... A61M 1/962; A61M 2202/0496; A61M 2210/1092; A61M 2210/1096;
(Continued)

(56) References Cited

U.S. PATENT DOCUMENTS

| 670,602 A | 3/1901 | Baker |
|---|---|---|
| 1,032,841 A | 7/1912 | Koenig |

(Continued)

FOREIGN PATENT DOCUMENTS

| AU | 2018216821 A1 | 8/2019 |
|---|---|---|
| CA | 2165286 C | 9/1999 |

(Continued)

OTHER PUBLICATIONS

US 9,908,683 B2, 03/2018, Sandhausen et al. (withdrawn)
(Continued)

*Primary Examiner* — Leslie A Lopez
*Assistant Examiner* — Jihad Dakkak
(74) *Attorney, Agent, or Firm* — Dorsey & Whitney LLP

(57) ABSTRACT

In an embodiment, a fluid collection device includes a fluid impermeable barrier that at least partially defines a chamber. The fluid impermeable barrier also defines an opening extending therethrough that is configured to be positioned adjacent to a female urethra or have a male urethra positioned therethrough. The fluid collection device also includes a channel extending between an inlet and outlet thereof. The inlet is configured to be in fluid communication with a gas source and the outlet is configured to be in fluid communication with a fluid storage container. The outlet is positioned downstream from the inlet. The channel also defines at least one aperture or passageway therein that allows an interior of the channel to be in fluid communication with the rest of the chamber.

19 Claims, 8 Drawing Sheets

(52) U.S. Cl.
CPC .............. *A61M 2202/0496* (2013.01); *A61M 2210/1092* (2013.01); *A61M 2210/1096* (2013.01)

(58) Field of Classification Search
CPC ... A61M 1/60–1/69; A61M 1/70–1/79; A61M 1/80–1/895; A61M 1/804; A61F 5/44; A61F 5/443; A61F 5/4401; A61F 5/4404; A61F 5/4408; A61F 5/451; A61F 5/453; A61F 5/455
See application file for complete search history.

(56) References Cited

U.S. PATENT DOCUMENTS

| | | |
|---|---|---|
| 1,178,644 A | 4/1916 | Johnson |
| 1,742,080 A | 12/1929 | Jones |
| 1,979,899 A | 11/1934 | OBrien et al. |
| 2,262,772 A * | 11/1941 | Larsen ............... A61M 11/06 55/458 |
| 2,326,881 A | 8/1943 | Packer |
| 2,379,346 A | 6/1945 | Farrell |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A * | 1/1961 | Duke ............... A61G 9/006 604/149 |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,233,025 A | 11/1980 | Larson et al. |
| 4,233,978 A | 11/1980 | Hickey |
| 4,246,901 A | 1/1981 | Frosch et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,352,356 A | 10/1982 | Tong |
| 4,360,933 A | 11/1982 | Kimura et al. |
| 4,365,363 A | 12/1982 | Windauer |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt, Jr. et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart, III |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |

(56) References Cited

U.S. PATENT DOCUMENTS

| | | |
|---|---|---|
| 5,045,283 A | 9/1991 | Patel |
| 5,049,144 A | 9/1991 | Payton |
| 5,053,339 A | 10/1991 | Patel |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,312,383 A | 5/1994 | Kubalak |
| 5,318,550 A | 6/1994 | Cermak et al. |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn, III et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,865,378 A | 2/1999 | Hollinshead et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,039,060 A * | 3/2000 | Rower ............... A61F 5/442 604/277 |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,248,096 B1 | 6/2001 | Dwork et al. |
| 6,263,887 B1 | 7/2001 | Dunn |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,428,521 B1 | 8/2002 | Droll |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,685,684 B1 | 2/2004 | Falconer |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,585,293 B2 * | 9/2009 | Vermaak ............... A61B 10/007 604/327 |
| 7,588,560 B1 | 9/2009 | Dunlop |
| 7,665,359 B2 | 2/2010 | Barber |
| 7,682,347 B2 | 3/2010 | Parks et al. |

(56) References Cited

U.S. PATENT DOCUMENTS

| | | |
|---|---|---|
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns, Jr. et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 * | 4/2017 | Locke .................. A61M 1/912 |
| D789,522 S | 6/2017 | Burgess et al. |
| 9,687,849 B2 | 6/2017 | Bruno et al. |
| 9,694,949 B2 | 7/2017 | Hendricks et al. |
| 9,713,547 B2 | 7/2017 | Lee et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 * | 3/2019 | Sanchez .................. A61F 5/455 |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B2 | 10/2020 | Harrison |
| D901,214 S | 11/2020 | Hu |
| 10,857,025 B2 * | 12/2020 | Davis .................. A61F 5/4408 |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |

(56) References Cited

U.S. PATENT DOCUMENTS

| | | |
|---|---|---|
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,179,506 B2 | 11/2021 | Barr et al. |
| 11,226,376 B2 | 1/2022 | Yamauchi et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,426,303 B2 | 8/2022 | Davis et al. |
| 11,529,252 B2 | 12/2022 | Glithero et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0269439 A1* | 11/2006 | White ............... C02F 1/686 422/243 |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1* | 9/2007 | Watt ............... A61M 27/00 602/42 |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge, II et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1* | 3/2011 | Weig ............... A61F 5/451 604/319 |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |

(56) References Cited

U.S. PATENT DOCUMENTS

| | | |
|---|---|---|
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0005647 A1 | 1/2014 | Shuffler et al. |
| 2014/0031774 A1 | 1/2014 | Bengtson |
| 2014/0157499 A1 | 6/2014 | Suzuki et al. |
| 2014/0171889 A1* | 6/2014 | Hopman ................ A61M 1/82 604/321 |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1* | 1/2017 | Minskoff ................ A61M 1/78 |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ................ A61F 5/4404 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ................ A61F 5/455 |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | McCourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |

(56) References Cited

U.S. PATENT DOCUMENTS

| | | |
|---|---|---|
| 2021/0009323 A1 | 1/2021 | Markarian et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104981 A1 | 4/2022 | Jones |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0248836 A1 | 8/2022 | Cagle et al. |
| 2022/0257407 A1 | 8/2022 | Johannes et al. |
| 2022/0265462 A1 | 8/2022 | Alder et al. |
| 2022/0273482 A1 | 9/2022 | Johannes et al. |
| 2022/0280357 A1 | 9/2022 | Jagannathan et al. |
| 2022/0313222 A1 | 10/2022 | Austermann et al. |
| 2022/0313474 A1 | 10/2022 | Kriscovich et al. |
| 2022/0354685 A1 | 11/2022 | Davis et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0062944 A1 | 3/2023 | Vollenberg et al. |
| 2023/0062994 A1 | 3/2023 | Ecklund et al. |
| 2023/0089032 A1 | 3/2023 | Hughett et al. |
| 2023/0105001 A1 | 4/2023 | Whittome et al. |
| 2023/0138269 A1 | 5/2023 | Abdelal et al. |
| 2023/0145365 A1 | 5/2023 | Martin et al. |
| 2023/0277362 A1 | 9/2023 | Davis et al. |

FOREIGN PATENT DOCUMENTS

| | | | |
|---|---|---|---|
| CA | 2354132 A1 | 6/2000 | |
| CA | 2488867 C | 8/2007 | |
| CA | 3050918 A1 | 8/2018 | |
| CA | 3098571 A1 | 11/2019 | |
| CN | 2269203 Y | 12/1997 | |
| CN | 1332620 A | 1/2002 | |
| CN | 1533755 A | 10/2004 | |
| CN | 1602825 A | 4/2005 | |
| CN | 1720888 A | 1/2006 | |
| CN | 2936204 Y | 8/2007 | |
| CN | 101262836 A | 9/2008 | |
| CN | 101522148 A | 9/2009 | |
| CN | 102159159 A | 8/2011 | |
| CN | 202184840 U | 4/2012 | |
| CN | 102481441 A | 5/2012 | |
| CN | 202463712 U | 10/2012 | |
| CN | 103533968 A | 1/2014 | |
| CN | 103717180 A | 4/2014 | |
| CN | 204562697 U | 8/2015 | |
| CN | 105411783 A | 3/2016 | |
| CN | 105451693 A | 3/2016 | |
| CN | 205849719 U | 1/2017 | |
| CN | 107847384 A | 3/2018 | |
| CN | 107920912 A | 4/2018 | |
| CN | 209285902 U | 8/2019 | |
| CN | 110381883 A | 10/2019 | |
| CN | 211198839 U | 8/2020 | |
| CN | 112566550 A | 3/2021 | |
| CN | 112603184 A | 4/2021 | |
| CN | 114007493 A | 2/2022 | |
| CN | 114375187 A | 4/2022 | |
| CN | 116096332 A | 5/2023 | |
| DE | 1516466 A1 | 6/1969 | |
| DE | 2721330 A1 | 11/1977 | |
| DE | 2742298 A1 | 3/1978 | |
| DE | 9407554.9 U1 | 5/1995 | |
| DE | 4443710 A1 | 6/1995 | |
| DE | 4416094 A1 | 11/1995 | |
| DE | 4236097 C2 | 10/1996 | |
| DE | 19619597 A1 | 11/1997 | |
| DE | 102005037762 B3 | 9/2006 | |
| DE | 102011103783 A1 | 12/2012 | |
| DE | 202015104597 U1 | 7/2016 | |
| DK | 9600118 | 11/1996 | |
| EP | 0032138 A2 | 7/1981 | |
| EP | 0066070 B1 | 12/1982 | |
| EP | 0274753 A2 | 7/1988 | |
| EP | 0119143 B1 | 11/1988 | |
| EP | 0483592 A1 | 5/1992 | |
| EP | 0610638 A1 * | 8/1994 | ............... A61F 5/44 |
| EP | 0613355 A1 | 9/1994 | |
| EP | 0613355 B1 | 1/1997 | |
| EP | 0787472 A1 | 8/1997 | |
| EP | 0966936 A1 | 12/1999 | |
| EP | 0987293 A1 | 3/2000 | |
| EP | 1063953 A1 | 1/2001 | |
| EP | 0653928 B1 | 10/2002 | |
| EP | 1332738 A1 | 8/2003 | |
| EP | 1382318 A1 | 1/2004 | |
| EP | 1089684 B1 | 10/2004 | |
| EP | 1616542 A1 | 1/2006 | |
| EP | 1382318 B1 | 5/2006 | |
| EP | 1063953 B1 | 1/2007 | |
| EP | 1872752 A1 | 1/2008 | |
| EP | 2180907 A1 | 5/2010 | |
| EP | 2380532 A1 | 10/2011 | |
| EP | 2389908 A1 | 11/2011 | |
| EP | 2601916 A1 | 6/2013 | |
| EP | 2676643 A1 | 12/2013 | |
| EP | 2997950 A2 | 3/2016 | |
| EP | 2879534 B1 | 3/2017 | |
| EP | 3424471 A1 | 1/2019 | |
| EP | 3169292 B1 | 11/2019 | |
| EP | 3753492 A1 | 12/2020 | |
| EP | 3788992 A1 | 3/2021 | |
| EP | 3576689 B1 | 3/2022 | |
| EP | 3752110 B1 | 3/2022 | |

(56) References Cited

FOREIGN PATENT DOCUMENTS

| | | |
|---|---|---|
| EP | 4025163 A1 | 7/2022 |
| EP | 3463180 B1 | 3/2023 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 3087938 B2 | 9/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |

(56) References Cited

FOREIGN PATENT DOCUMENTS

| | | |
|---|---|---|
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021086868 A1 | 5/2021 |
| WO | 2021094352 A1 | 5/2021 |
| WO | 2021094639 A1 | 5/2021 |
| WO | 2021102296 A1 | 5/2021 |
| WO | 2021138411 A1 | 7/2021 |
| WO | 2021138414 A1 | 7/2021 |
| WO | 2021155206 A1 | 8/2021 |
| WO | 2021173436 A1 | 9/2021 |
| WO | 2021195384 A1 | 9/2021 |
| WO | 2021207621 A1 | 10/2021 |
| WO | 2021211568 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022076427 A2 | 4/2022 |
| WO | 2022086898 A1 | 4/2022 |
| WO | 2022098536 A1 | 5/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022192188 A1 | 9/2022 |
| WO | 2022192347 A1 | 9/2022 |
| WO | 2023014639 A1 | 2/2023 |
| WO | 2023014641 A1 | 2/2023 |
| WO | 2023034453 A1 | 3/2023 |
| WO | 2023038945 A1 | 3/2023 |
| WO | 2023038950 A1 | 3/2023 |
| WO | 2023049175 A1 | 3/2023 |
| WO | 2023086394 A1 | 5/2023 |
| WO | 2023191764 A1 | 10/2023 |

OTHER PUBLICATIONS

Corrected Notice of Allowability for U.S. Appl. No. 15/612,325 dated Mar. 17, 2021.
Issue Notification for U.S. Appl. No. 15/171,968 dated Mar. 3, 2021.
Issue Notification for U.S. Appl. No. 15/612,325 dated Mar. 24, 2021.
Non-Final Office Action for U.S. Appl. No. 17/088,272 dated Jan. 25, 2021.
Notice of Allowance for U.S. Appl. No. 15/171,968 dated Feb. 16, 2021.
Notice of Allowance for U.S. Appl. No. 15/612,325 dated Feb. 19, 2021.
Notice of Allowance for U.S. Appl. No. 29/694,002 dated Jan. 29, 2021.
Notice to File Missing Parts for U.S. Appl. No. 17/179,116 dated Mar. 3, 2021.
U.S. Appl. No. 17/179,116, filed Feb. 18, 2021.
U.S. Appl. No. 63/146,946, filed Feb. 8, 2021.
U.S. Appl. No. 63/147,299, filed Feb. 9, 2021.

(56) References Cited

OTHER PUBLICATIONS

U.S. Appl. No. 63/148,723, filed Feb. 12, 2021.
Memorandum Order, Feb. 2021, 14 pgs.
Decision Granting Institution of Inter Partes Review for U.S. Pat. No. 8,287,508, Case No. 2020-01426, Feb. 17, 2021, 39 pages.
Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Non-Final Office Action for U.S. Appl. No. 14/722,613 dated Jun. 13, 2019.
Non-Final Office Action for U.S. Appl. No. 14/947,759 dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 29/624,661 dated Jul. 18, 2019.
Non-Final Office Action for U.S. Appl. No. 29/694,002 dated Jun. 24, 2020.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Oct. 16, 2020.
Notice of Allowance for U.S. Appl. No. 15/612,325 dated Jan. 21, 2021.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.

(56) References Cited

OTHER PUBLICATIONS

U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,889, filed May 29, 2019.
U.S. Appl. No. 62/873,045, filed Jul. 11, 2019.
U.S. Appl. No. 62/873,048, filed Jul. 11, 2019.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/134,287, filed Jan. 6, 2021.
U.S. Appl. No. 63/134,632, filed Jan. 7, 2021.
Defendant and Counterclaim Plaintiff Sage Products, LLC's Answer, Defenses, and Counterclaims to Plaintiff's Amended Complaint, Nov. 1, 2019.
Sage's Initial Invalidity Contentions Regarding U.S. Pat. No. 8,287,508; U.S. Pat. No. 10,226,375; and U.S. Pat. No. 10,390,989, May 29, 2020, 193 pages.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, Case No. 19-1508-MN, 7 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical. com, https://www.vitalitymedical.com/hollister-retracted-penis-pouch.html last accessed Jun. 24, 2020, 6 pages.
MacAulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
PureWick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.

(56) References Cited

OTHER PUBLICATIONS

Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 16/905,400 dated Apr. 6, 2021.
Notice of Allowance for U.S. Appl. No. 14/952,591 dated Apr. 5, 2021.
Notice of Allowance for U.S. Appl. No. 29/624,661 dated Apr. 28, 2021.
Notice of Allowance for U.S. Appl. No. 29/694,002 dated Apr. 29, 2021.
Boehringer CareDry System—Second Generation for Non-Invasive Urinary Management for Females, Mar. 2021, 3 pgs.
International Search Report and Written Opinion from International Application No. PCT/US2021/027917 dated Aug. 19, 2021.
International Search Report and Written Opinion from International Application No. PCT/US2021/039866 dated Oct. 7, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
International Search Report and Written Opinion from International Application No. PCT/US2022/044107 dated Dec. 23, 2022.
Issue Notification for U.S. Appl. No. 14/952,591 dated Jul. 28, 2021.
Issue Notification for U.S. Appl. No. 16/905,400 dated Nov. 30, 2022.
Issue Notification for U.S. Appl. No. 17/088,272 dated Jun. 15, 2022.
Issue Notification for U.S. Appl. No. 17/330,657 dated Jun. 22, 2022.
Issue Notification for U.S. Appl. No. 29/624,661 dated Aug. 4, 2021.
Advisory Action for U.S. Appl. No. 16/433,773 dated Feb. 15, 2023.
Advisory Action for U.S. Appl. No. 16/452,258 dated Oct. 26, 2022.
Advisory Action for U.S. Appl. No. 16/478,180 dated Sep. 21, 2022.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/904,868 dated Jun. 15, 2022.
Advisory Action for U.S. Appl. No. 16/905,400 dated Feb. 16, 2022.
Advisory Action for U.S. Appl. No. 16/905,400 dated Jun. 9, 2021.
Advisory Action for U.S. Appl. No. 17/662,700 dated Jan. 30, 2023.
Corrected Notice of Allowability for U.S. Appl. No. 17/330,657 dated Dec. 9, 2021.
Final Office Action for U.S. Appl. No. 16/245,726 dated Nov. 25, 2022.
Final Office Action for U.S. Appl. No. 16/369,676 dated Dec. 5, 2022.
Final Office Action for U.S. Appl. No. 16/433,773 dated Oct. 25, 2022.
Final Office Action for U.S. Appl. No. 16/449,039 dated Aug. 1, 2022.
Final Office Action for U.S. Appl. No. 16/452,145 dated Mar. 25, 2022.
Final Office Action for U.S. Appl. No. 16/452,258 dated Jun. 14, 2022.
Final Office Action for U.S. Appl. No. 16/478,180 dated Jun. 22, 2022.
Final Office Action for U.S. Appl. No. 16/904,868 dated Mar. 10, 2022.
Final Office Action for U.S. Appl. No. 16/905,400 dated Dec. 9, 2021.
Final Office Action for U.S. Appl. No. 17/051,399 dated Mar. 9, 2023.
Final Office Action for U.S. Appl. No. 17/088,272 dated May 25, 2021.
Final Office Action for U.S. Appl. No. 17/662,700 dated Sep. 30, 2022.
International Search Report and Written Opinion from International Application No. PCT/IB2021/057173 dated Nov. 5, 2021.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/057562 dated Jan. 27, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/026607 dated Jul. 29, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/049404 dated Jan. 18, 2022.

(56) References Cited

OTHER PUBLICATIONS

International Search Report and Written Opinion from International Application No. PCT/US2021/051456 dated Jan. 19, 2022.
International Search Report and Written Opinion from International Application No. PCT/US2021/053593 dated Apr. 11, 2022.
International Search Report and Written Opinion from International Application No. PCT/US2021/055515 dated Jan. 28, 2022.
International Search Report and Written Opinion from International Application No. PCT/US2021/056566 dated Feb. 11, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.
International Search Report and Written Opinion from International Application No. PCT/US2022/011281 dated Apr. 25, 2022.
International Search Report and Written Opinion from International Application No. PCT/US2022/011419 dated Jun. 7, 2022.
International Search Report and Written Opinion from International Application No. PCT/US2022/011421 dated Jun. 13, 2022.
International Search Report and Written Opinion from International Application No. PCT/US2022/012794 dated May 3, 2022.
International Search Report and Written Opinion from International Application No. PCT/US2022/014285 dated Sep. 28, 2022.
International Search Report and Written Opinion from International Application No. PCT/US2022/014749 dated Sep. 28, 2022.
International Search Report and Written Opinion from International Application No. PCT/US2022/015026 dated Oct. 31, 2022.
International Search Report and Written Opinion from International Application No. PCT/US2022/015045 dated Sep. 9, 2022.
International Search Report and Written Opinion from International Application No. PCT/US2022/015073 dated Sep. 8, 2022.
International Search Report and Written Opinion from International Application No. PCT/US2022/015418 dated Nov. 11, 2022.
International Search Report and Written Opinion from International Application No. PCT/US2022/015420 dated Nov. 18, 2022.
International Search Report and Written Opinion from International Application No. PCT/US2022/015471 dated May 16, 2022.
International Search Report and Written Opinion from International Application No. PCT/US2022/015492 dated Apr. 26, 2022.
International Search Report and Written Opinion from International Application No. PCT/US2022/015781 dated May 6, 2022.
International Search Report and Written Opinion from International Application No. PCT/US2022/016942 dated Jun. 8, 2022.
International Search Report and Written Opinion from International Application No. PCT/US2022/018159 dated Dec. 12, 2022.
International Search Report and Written Opinion from International Application No. PCT/US2022/018170 dated May 31, 2022.
International Search Report and Written Opinion from International Application No. PCT/US2022/019254 dated Jun. 7, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
International Search Report and Written Opinion from International Application No. PCT/US2022/022111 dated Oct. 26, 2022.
International Search Report and Written Opinion from International Application No. PCT/US2022/023594 dated Jul. 12, 2022.
International Search Report and Written Opinion from International Application No. PCT/US2022/026667 dated Aug. 22, 2022.
International Search Report and Written Opinion from International Application No. PCT/US2022/030685 dated Oct. 31, 2022.
International Search Report and Written Opinion from International Application No. PCT/US2022/031032 dated Sep. 9, 2022.
International Search Report and Written Opinion from International Application No. PCT/US2022/032424 dated Oct. 11, 2022.
International Search Report and Written Opinion from International Application No. PCT/US2022/034457 dated Oct. 12, 2022.
International Search Report and Written Opinion from International Application No. PCT/US2022/034744 dated Dec. 9, 2022.
International Search Report and Written Opinion from International Application No. PCT/US2022/039018 dated Jan. 10, 2023.
International Search Report and Written Opinion from International Application No. PCT/US2022/039022 dated Jan. 10, 2023.
International Search Report and Written Opinion from International Application No. PCT/US2022/039711 dated Jan. 12, 2023.
International Search Report and Written Opinion from International Application No. PCT/US2022/039714 dated Nov. 22, 2022.
International Search Report and Written Opinion from International Application No. PCT/US2022/042719 dated Dec. 5, 2022.
International Search Report and Written Opinion from International Application No. PCT/US2022/042725 dated Dec. 19, 2022.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/433,773 dated Apr. 21, 2022.
Non-Final Office Action for U.S. Appl. No. 16/449,039 dated Dec. 8, 2021.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Dec. 20, 2022.
Non-Final Office Action for U.S. Appl. No. 16/478,180 dated Oct. 22, 2021.
Non-Final Office Action for U.S. Appl. No. 16/899,956 dated Sep. 2, 2021.
Non-Final Office Action for U.S. Appl. No. 16/904,868 dated Oct. 5, 2021.
Non-Final Office Action for U.S. Appl. No. 16/905,400 dated Apr. 27, 2022.
Non-Final Office Action for U.S. Appl. No. 16/905,400 dated Jul. 22, 2021.
Non-Final Office Action for U.S. Appl. No. 17/330,657 dated Aug. 11, 2021.
Non-Final Office Action for U.S. Appl. No. 17/444,792 dated Feb. 10, 2023.
Non-Final Office Action for U.S. Appl. No. 17/451,345 dated Dec. 7, 2022.
Non-Final Office Action for U.S. Appl. No. 17/662,700 dated Jul. 22, 2022.
Non-Final Office Action for U.S. Appl. No. 29/741,751 dated Jan. 18, 2022.
Notice of Allowance for U.S. Appl. No. 14/952,591 dated Jul. 8, 2021.
Notice of Allowance for U.S. Appl. No. 16/449,039 dated Dec. 15, 2022.
Notice of Allowance for U.S. Appl. No. 16/899,956 dated Apr. 19, 2022.
Notice of Allowance for U.S. Appl. No. 16/899,956 dated Aug. 10, 2022.
Notice of Allowance for U.S. Appl. No. 16/899,956 dated Dec. 1, 2022.
Notice of Allowance for U.S. Appl. No. 16/899,956 dated Dec. 29, 2021.
Notice of Allowance for U.S. Appl. No. 16/905,400 dated Aug. 17, 2022.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Mar. 16, 2022.
Notice of Allowance for U.S. Appl. No. 17/330,657 dated Nov. 26, 2021.

(56) References Cited

OTHER PUBLICATIONS

Notice of Allowance for U.S. Appl. No. 17/461,036 dated Feb. 22, 2023.
Notice of Allowance for U.S. Appl. No. 17/461,036 dated Oct. 6, 2022.
Notice of Allowance for U.S. Appl. No. 17/663,046 dated Jan. 30, 2023.
Notice of Allowance for U.S. Appl. No. 29/741,751 dated Jun. 9, 2022.
Restriction Requirement for U.S. Appl. No. 16/433,773 dated Dec. 7, 2021.
Restriction Requirement for U.S. Appl. No. 16/478,180 dated May 25, 2021.
Restriction Requirement for U.S. Appl. No. 17/446,256 dated Jan. 23, 2023.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 16/245,726, filed Jan. 11, 2019.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036, filed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/164,800, filed Feb. 6, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/853,279, filed May 28, 2019.
U.S. Appl. No. 62/864,656, filed Jun. 21, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/030,685, filed May 27, 2020.
U.S. Appl. No. 63/047,374, filed Jul. 2, 2020.
U.S. Appl. No. 63/067,542, filed Aug. 19, 2020.
U.S. Appl. No. 63/073,545, filed Sep. 2, 2020.
U.S. Appl. No. 63/073,553, filed Sep. 2, 2020.
U.S. Appl. No. 63/094,498, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,450, filed Jan. 6, 2021.
U.S. Appl. No. 63/134,631, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/147,013, filed Feb. 8, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.

(56) References Cited

OTHER PUBLICATIONS

U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
U.S. Appl. No. 63/308,190, filed Feb. 9, 2022.
"External Urine Management for Female Anatomy", https://www.stryker.com/us/en/sage/products/sage-primafit.html, Jul. 2020, 4 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia, Aug. 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Tsipenyuk, et al., "Use of biomimetic hexagonal surface texture in friction against lubricated skin", Journal of The Royal Society—Interface, 2014, pp. 1-6.
Advisory Action for U.S. Appl. No. 16/245,726 dated Apr. 19, 2023.
Advisory Action for U.S. Appl. No. 16/369,676 dated Mar. 24, 2023.
Advisory Action for U.S. Appl. No. 16/478,180 dated Sep. 7, 2023.
Advisory Action for U.S. Appl. No. 17/444,792 dated Aug. 25, 2023.
Final Office Action for U.S. Appl. No. 16/369,676 dated Aug. 31, 2023.
Final Office Action for U.S. Appl. No. 16/478,180 dated May 31, 2023.
Final Office Action for U.S. Appl. No. 17/051,550 dated May 23, 2023.
Final Office Action for U.S. Appl. No. 17/051,585 dated Jul. 27, 2023.
Final Office Action for U.S. Appl. No. 17/444,792 dated Jun. 15, 2023.
Final Office Action for U.S. Appl. No. 17/448,811 dated Aug. 3, 2023.
Final Office Action for U.S. Appl. No. 17/451,345 dated May 3, 2023.
Final Office Action for U.S. Appl. No. 17/655,464 dated Sep. 1, 2023.
International Search Report and Written Opinion from International Application No. PCT/US2022/041085 dated Mar. 16, 2023.
International Search Report and Written Opinion from International Application No. PCT/US2022/041688 dated Nov. 21, 2022.
International Search Report and Written Opinion from International Application No. PCT/US2022/043818 dated Mar. 24, 2023.
International Search Report and Written Opinion from International Application No. PCT/US2022/044208 dated May 8, 2023.
International Search Report and Written Opinion from International Application No. PCT/US2022/044212 dated Jan. 20, 2023.
International Search Report and Written Opinion from International Application No. PCT/US2022/044243 dated Feb. 24, 2023.
International Search Report and Written Opinion from International Application No. PCT/US2022/049300 dated Jun. 6, 2023.
International Search Report and Written Opinion from International Application No. PCT/US2022/050909 dated Jul. 24, 2023.
International Search Report and Written Opinion from International Application No. PCT/US2023/012696 dated Jul. 6, 2023.
Issue Notification for U.S. Appl. No. 16/899,956 dated Mar. 29, 2023.
Non-Final Office Action for U.S. Appl. No. 16/433,773 dated Apr. 11, 2023.
Non-Final Office Action for U.S. Appl. No. 16/449,039 dated Apr. 27, 2023.
Non-Final Office Action for U.S. Appl. No. 16/452,145 dated Mar. 28, 2023.
Non-Final Office Action for U.S. Appl. No. 16/452,258 dated Apr. 26, 2023.
Non-Final Office Action for U.S. Appl. No. 16/904,868 dated Mar. 15, 2023.
Non-Final Office Action for U.S. Appl. No. 17/051,399 dated Aug. 18, 2023.
Non-Final Office Action for U.S. Appl. No. 17/051,585 dated Mar. 29, 2023.
Non-Final Office Action for U.S. Appl. No. 17/179,116 dated Mar. 24, 2023.
Non-Final Office Action for U.S. Appl. No. 17/326,980 dated Jul. 11, 2023.
Non-Final Office Action for U.S. Appl. No. 17/446,256 dated Apr. 13, 2023.
Non-Final Office Action for U.S. Appl. No. 17/446,654 dated Sep. 8, 2023.
Non-Final Office Action for U.S. Appl. No. 17/448,811 dated Mar. 1, 2023.
Non-Final Office Action for U.S. Appl. No. 17/450,864 dated May 10, 2023.
Non-Final Office Action for U.S. Appl. No. 17/451,354 dated May 3, 2023.
Non-Final Office Action for U.S. Appl. No. 17/453,260 dated Mar. 14, 2023.
Non-Final Office Action for U.S. Appl. No. 17/501,591 dated Apr. 25, 2023.
Non-Final Office Action for U.S. Appl. No. 17/646,771 dated Jul. 5, 2023.
Non-Final Office Action for U.S. Appl. No. 17/653,137 dated Apr. 7, 2023.
Non-Final Office Action for U.S. Appl. No. 17/655,464 dated Mar. 14, 2023.
Non-Final Office Action for U.S. Appl. No. 17/657,474 dated Sep. 12, 2023.
Non-Final Office Action for U.S. Appl. No. 17/661,090 dated Jul. 6, 2023.
Non-Final Office Action for U.S. Appl. No. 17/663,330 dated Jun. 29, 2023.

(56) References Cited

OTHER PUBLICATIONS

Non-Final Office Action for U.S. Appl. No. 17/664,487 dated Jun. 8, 2023.
Non-Final Office Action for U.S. Appl. No. 18/139,523 dated Aug. 17, 2023.
Non-Final Office Action for U.S. Appl. No. 18/140,751 dated Sep. 14, 2023.
Notice of Allowance for U.S. Appl. No. 16/245,726 dated Jul. 6, 2023.
Notice of Allowance for U.S. Appl. No. 17/051,554 dated Jul. 6, 2023.
Notice of Allowance for U.S. Appl. No. 17/461,036 dated Jun. 30, 2023.
Notice of Allowance for U.S. Appl. No. 17/662,700 dated Jul. 28, 2023.
Notice of Allowance for U.S. Appl. No. 17/662,700 dated Mar. 28, 2023.
Notice of Allowance for U.S. Appl. No. 18/299,788 dated Jul. 24, 2023.
Restriction Requirement for U.S. Appl. No. 17/326,980 dated Mar. 20, 2023.
Restriction Requirement for U.S. Appl. No. 17/645,821 dated Jul. 12, 2023.
Restriction Requirement for U.S. Appl. No. 17/646,771 dated Apr. 6, 2023.
Restriction Requirement for U.S. Appl. No. 17/657,474 dated Jun. 30, 2023.
Text Messages to Lorena Eckert Re Prototype PureWick Holder dated Apr. 16, 2022.
U.S. Appl. No. 17/664,487, filed May 23, 2022.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/548,152, filed Aug. 28, 2023.
U.S. Appl. No. 18/549,387, filed Sep. 7, 2023.
U.S. Appl. No. 63/150,640, filed Feb. 18, 2021.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.

"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 dated Dec. 29, 2023.
Advisory Action for U.S. Appl. No. 16/904,868 dated Jan. 2, 2024.
Advisory Action for U.S. Appl. No. 17/051,585 dated Oct. 17, 2023.
Advisory Action for U.S. Appl. No. 17/179,116 dated Jan. 8, 2024.
Advisory Action for U.S. Appl. No. 17/446,256 dated Dec. 8, 2023.
Advisory Action for U.S. Appl. No. 17/448,811 dated Nov. 15, 2023.
Advisory Action for U.S. Appl. No. 17/451,345 dated Oct. 20, 2023.
Advisory Action for U.S. Appl. No. 17/453,260 dated Dec. 22, 2023.
Advisory Action for U.S. Appl. No. 17/653,137 dated Dec. 1, 2023.
Advisory Action for U.S. Appl. No. 17/655,464 dated Dec. 13, 2023.
Communication of Notice of Opposition of European Application No. 17807547.9 mailed Jan. 5, 2024.
Corrected Notice of Allowability for U.S. Appl. No. 16/369,676 dated Dec. 7, 2023.
Final Office Action for U.S. Appl. No. 16/433,773 dated Oct. 10, 2023.
Final Office Action for U.S. Appl. No. 16/449,039 dated Nov. 21, 2023.
Final Office Action for U.S. Appl. No. 16/452,258 dated Dec. 21, 2023.
Final Office Action for U.S. Appl. No. 16/904,868 dated Nov. 2, 2023.
Final Office Action for U.S. Appl. No. 17/051,399 dated Jan. 8, 2024.
Final Office Action for U.S. Appl. No. 17/179,116 dated Oct. 31, 2023.
Final Office Action for U.S. Appl. No. 17/446,256 dated Sep. 19, 2023.
Final Office Action for U.S. Appl. No. 17/450,864 dated Dec. 28, 2023.
Final Office Action for U.S. Appl. No. 17/451,354 dated Oct. 30, 2023.
Final Office Action for U.S. Appl. No. 17/453,260 dated Oct. 5, 2023.
Final Office Action for U.S. Appl. No. 17/501,591 dated Nov. 14, 2023.
Final Office Action for U.S. Appl. No. 17/646,771 dated Dec. 21, 2023.
Final Office Action for U.S. Appl. No. 17/653,137 dated Sep. 21, 2023.
Final Office Action for U.S. Appl. No. 17/661,090 dated Dec. 11, 2023.
Final Office Action for U.S. Appl. No. 17/663,330 dated Dec. 12, 2023.
Final Office Action for U.S. Appl. No. 17/664,487 dated Jan. 4, 2024.
Final Office Action for U.S. Appl. No. 18/139,523 dated Dec. 22, 2023.
Final Office Action for U.S. Appl. No. 18/140,751 dated Jan. 17, 2024.
Final Office Action for U.S. Appl. No. 18/164,800 dated Dec. 6, 2023.
International Search Report and Written Opinion from International Application No. PCT/US2023/018474 dated Sep. 11, 2023.

(56) References Cited

OTHER PUBLICATIONS

International Search Report and Written Opinion from International Application No. PCT/US2023/024805 dated Dec. 14, 2023.
Issue Notification for U.S. Appl. No. 16/245,726 dated Oct. 18, 2023.
Issue Notification for U.S. Appl. No. 17/461,036 dated Oct. 11, 2023.
Issue Notification for U.S. Appl. No. 17/663,046 dated Dec. 20, 2023.
Non-Final Office Action for U.S. Appl. No. 16/452,145 dated Nov. 2, 2023.
Non-Final Office Action for U.S. Appl. No. 16/478,180 dated Nov. 7, 2023.
Non-Final Office Action for U.S. Appl. No. 17/051,585 dated Jan. 8, 2024.
Non-Final Office Action for U.S. Appl. No. 17/051,600 dated Jan. 17, 2024.
Non-Final Office Action for U.S. Appl. No. 17/444,792 dated Nov. 17, 2023.
Non-Final Office Action for U.S. Appl. No. 17/448,811 dated Jan. 17, 2024.
Non-Final Office Action for U.S. Appl. No. 17/451,345 dated Jan. 17, 2024.
Non-Final Office Action for U.S. Appl. No. 17/453,560 dated Oct. 16, 2023.
Non-Final Office Action for U.S. Appl. No. 17/645,821 dated Oct. 25, 2023.
Non-Final Office Action for U.S. Appl. No. 17/653,137 dated Jan. 18, 2024.
Non-Final Office Action for U.S. Appl. No. 17/808,354 dated Nov. 28, 2023.
Non-Final Office Action for U.S. Appl. No. 18/140,163 dated Nov. 9, 2023.
Non-Final Office Action for U.S. Appl. No. 18/198,464 dated Dec. 7, 2023.
Notice of Allowance for U.S. Appl. No. 16/369,676 dated Nov. 14, 2023.
Notice of Allowance for U.S. Appl. No. 17/051,554 dated Oct. 18, 2023.
Notice of Allowance for U.S. Appl. No. 17/662,700 dated Nov. 15, 2023.
Notice of Allowance for U.S. Appl. No. 18/299,788 dated Nov. 6, 2023.
Restriction Requirement for U.S. Appl. No. 17/051,600 dated Sep. 21, 2023.
Restriction Requirement for U.S. Appl. No. 18/134,857 dated Oct. 23, 2023.
Submission in Opposition Proceedings for European Application No. 17807547.9 filed Jan. 10, 2024.
U.S. Appl. No. 17/451,719, filed Oct. 19, 2021.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 63/596,012, filed Nov. 3, 2023.
U.S. Appl. No. 63/608,553, filed Dec. 11, 2023.
Wikipedia Article, "Zylinder (Geometrie)", https://de.wikipedia.org/w/index.php?title=Zylinder (Geometrie)&oldid=154862081, version of Jun. 1, 2016, 7 pages.

\* cited by examiner

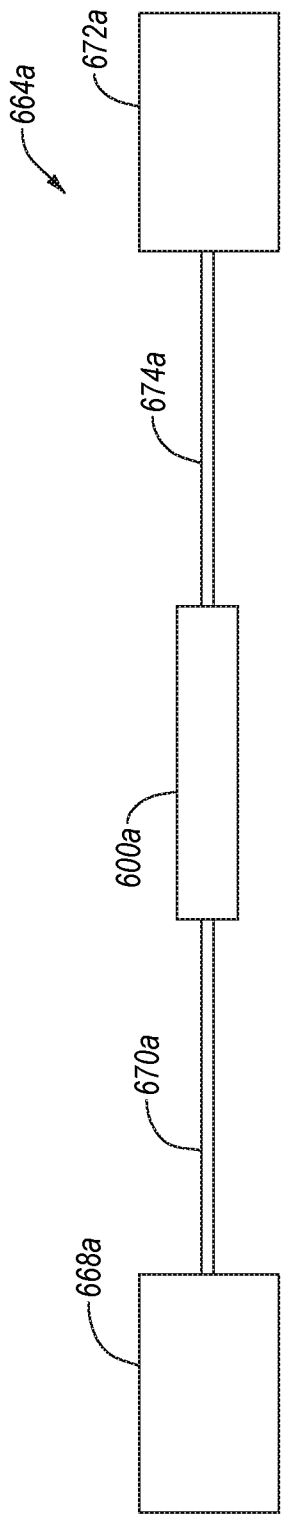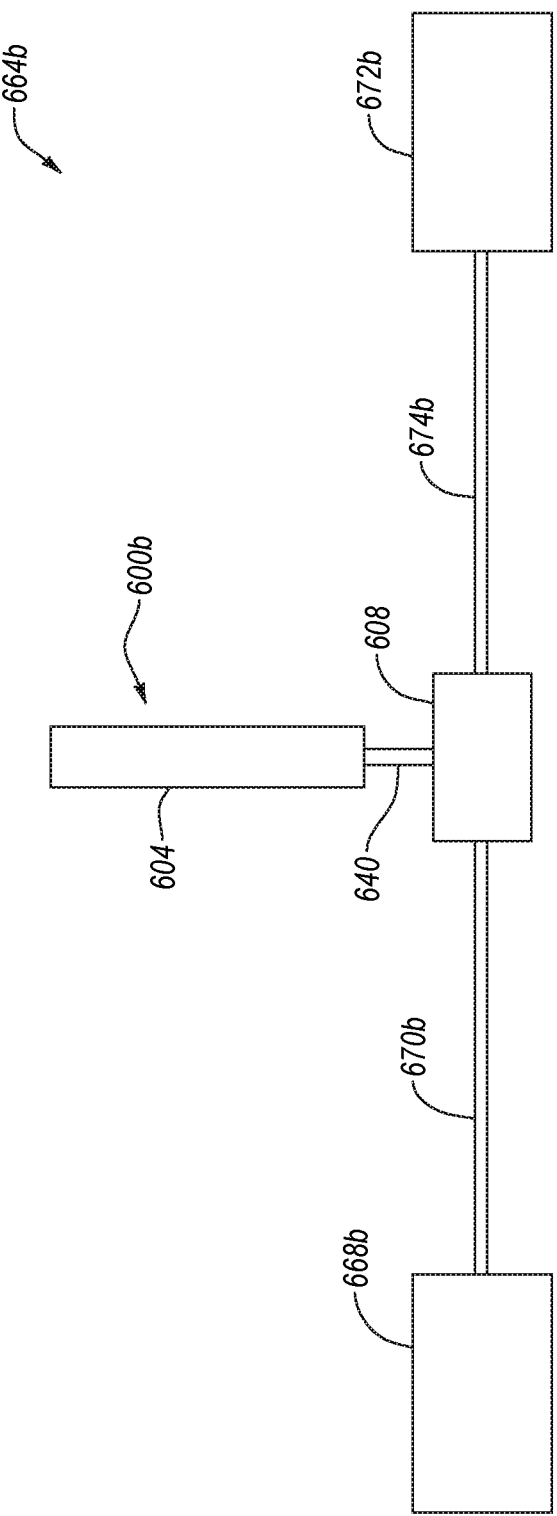

FLUID COLLECTION DEVICES, RELATED SYSTEMS, AND RELATED METHODS

CROSS-REFERENCE TO RELATED APPLICATIONS

This application is a U.S. Nationalization of PCT International Application No. PCT/US2019/029609 filed on 29 Apr. 2019, which claims priority to U.S. Provisional Application No. 62/665,331 filed on 1 May 2018, the disclosure of each of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are related to devices, systems, and methods of using fluid collection devices. In an embodiment, a fluid collection device is disclosed. The fluid collection device includes a fluid impermeable barrier at least partially defining a chamber. The fluid impermeable barrier also defines an opening extending therethrough. The opening is configured to be positioned adjacent to a female urethra or have a male urethra positioned therethrough. The fluid collection device also includes a channel defining and extending between an inlet and an outlet. The outlet is positioned downstream from the inlet. The inlet is configured to be in fluid communication with an gas source and the outlet is configured to be in fluid communication with a fluid storage container. The channel defines at least one aperture that allows an interior of the channel to be in fluid communication with the chamber.

In an embodiment, a fluid collection system is disclosed. The fluid collection system includes a gas source and a fluid storage container positioned downstream from the gas source. The fluid storage container is configured to hold a fluid. The fluid collection system also includes a fluid collection device spaced from the gas source and the fluid storage container. The fluid collection device includes a fluid impermeable barrier at least partially defining a chamber. The fluid impermeable barrier also defines an opening extending therethrough. The opening is configured to be positioned adjacent to a female urethra or have a male urethra positioned therethrough. The fluid collection device also includes a channel defining and extending between an inlet and an outlet. The outlet is positioned downstream from the inlet. The inlet is configured to be in fluid communication with a gas source and the outlet is configured to be in fluid communication with a fluid storage container. The channel defines at least one aperture that allows an interior of the channel to be in fluid communication with the chamber.

In an embodiment, a method to collect fluid is disclosed. The method includes positioning an opening of a fluid collection device adjacent to a female urethra or around a male urethra. The opening is defined by a fluid impermeable barrier of the fluid collection device. The method also includes receiving fluids from the female urethra or the male urethra into a chamber of the fluid collection device. The chamber of the fluid collection device is at least partially defined by the fluid impermeable barrier. The method further includes flowing gas from an inlet to an outlet of a channel of the fluid collection device that is effective to suction the fluids into the channel from the chamber via at least one aperture formed in the channel and push the fluids that enters the channel via the at least one aperture towards the outlet. The channel extends from the inlet to the outlet.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 6A is a schematic of a fluid collection system, according to an embodiment.

FIG. 6B is a schematic of a fluid collection system, according to an embodiment.

DETAILED DESCRIPTION

Embodiments disclosed herein are related to devices, systems, and methods of using fluid collection devices. In an embodiment, a fluid collection device includes a fluid impermeable barrier that at least partially defines a chamber. The fluid impermeable barrier also defines an opening extending therethrough that is configured to be positioned adjacent to a female urethra or have a male urethra positioned therethrough. The fluid collection device also includes a channel extending between an inlet and outlet thereof. The inlet is configured to be in fluid communication with (e.g., fluidly coupled to) a gas source. The inlet may be in direct fluid communication (e.g., directly attached to) or indirect fluid communication (e.g., via at least one tube) with the gas source. The outlet is configured to be in fluid communication with a fluid storage container. The outlet may be in direct fluid communication or indirect fluid communication (e.g., via at least one tube) to the fluid storage container. The outlet is positioned downstream from the inlet. The channel also defines at least one aperture therein that allows an interior of the channel to be in fluid communication with the rest of the chamber.

The fluid collection devices disclosed herein are configured to collect fluids from an individual. The fluids collected by the fluid collection devices can include urine. The fluids collected by the fluid collection devices can also include at least one of vagina discharge, penile discharge, reproductive fluids, blood, sweat, or other bodily fluids.

The fluid collection devices disclosed herein are configured to be used in fluid collection systems. The fluid collection systems disclosed herein include a gas source. Systems that include the gas source can, in some embodiments, resolve several problem associated with systems that include a vacuum source. For example, a system that includes a vacuum source draws fluids towards the vacuum source and deposits most of the fluids in a fluid storage container before the fluids can reach the vacuum source. However, a small quantity of fluids (e.g., vapor from the fluids) can still reach the vacuum source, which can contaminate and/or damage (e.g., rust) the vacuum source. Additionally, a large quantity of the fluids can reach the vacuum source when the fluid storage container is substantially full. However, a system that includes a gas source moves the fluids away from the gas source, thereby preventing contamination and/or damage. In another embodiment, systems that include a vacuum source cannot be used in environments that do not include an available vacuum source (e.g., the environment does not include a vacuum source or the vacuum source is being used). As such, systems that include a gas source can be used in environments that do not include an available vacuum source.

Figure 1:
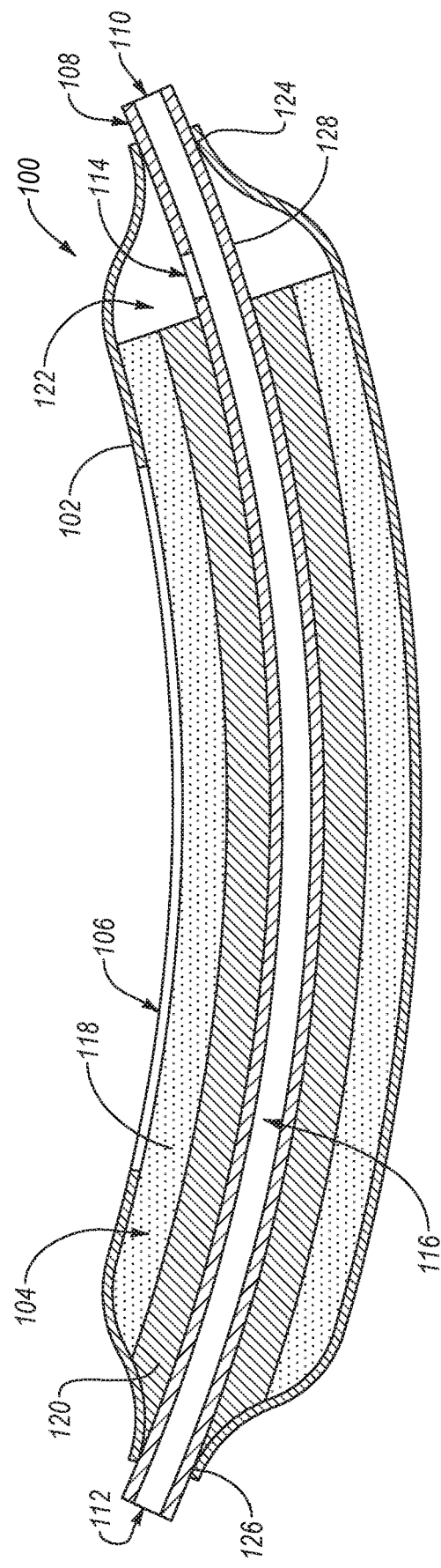
FIG. 1 is a schematic cross-sectional view of a fluid collection device, according to an embodiment.

FIG. 1 is a schematic cross-sectional view of a fluid collection device 100, according to an embodiment. The fluid collection device 100 is an example of a female fluid collection device 100 that is configured to receive fluids from a female. The fluid collection device 100 includes a fluid impermeable barrier 102. The fluid impermeable barrier 102 at least partially defines a chamber 104 and an opening 106. The opening 106 extends through the fluid impermeable barrier 102, thereby enabling fluids to enter the chamber 104. The opening 106 can be configured to be positioned adjacent to a female urethra. The fluid collection device 100 also includes a channel 108 that is at least partially disposed in the chamber 104. The channel 108 (e.g., a tube or a conduit) includes an inlet 110 and an outlet 112 positioned downstream from the inlet 110. The inlet 110 is configured to be in fluid communication with a gas source (not shown) and the outlet 112 is configured to be in fluid communication with a fluid storage container (not shown). The channel 108 defines at least one aperture 114 that allows an interior 116 of the channel 108 to be in fluid communication with the chamber 104. In the illustrated embodiment, the channel 108 is at least partially disposed and the aperture 114 is disposed in the chamber 104.

The fluid collection device 100 is configured to receive the fluids into the chamber 104 via the opening 106. For example, the opening 106 can exhibit an elongated shape that is configured to extend from a first location below the urethral opening (e.g., at or near the anus or the vaginal opening) to a second location above the urethral opening (e.g., at or near the clitoris or the pubic hair). The opening 106 can exhibit an elongated shape since the space between the legs of a female is relatively small when the legs of the female are closed thereby only permitting the flow of the fluids along a path that corresponds to the elongated shape of the opening 106. The opening 106 can exhibit a width that is measured transverse to the longitudinal direction that is at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 can exhibit a width that is greater than 50% of the circumference of the fluid collection device 100 since the continual flow of gas (e.g., atmospheric air, nitrogen, oxygen, etc.) through the channel 108 pulls the fluid into the channel 108. In some embodiments, the opening 106 may be vertically oriented (e.g., having a major axis that is generally parallel to the longitudinal axis of the device 100). In some embodiments, (not shown), the opening 106 may be horizontally oriented (e.g., having a major axis perpendicular to the longitudinal axis of the device 100). In an example, the fluid impermeable barrier 102 can be configured to be attached to the individual, such as adhesively attached (e.g., with a hydrogel adhesive) to the individual. According to an embodiment, a suitable adhesive is a hydrogel layer, such as those disclosed in U.S. Patent Application Publication No. 2017/0189225, the disclosure of which is incorporated herein by reference in its entirety.

The fluid impermeable barrier 102 is also configured to temporarily store the fluids in the chamber 104. For example, the fluid impermeable barrier 102 can be formed of any suitable fluid impermeable materials, such as a fluid impermeable polymer (e.g., silicone, polypropylene, polyethylene, polyethylene terephthalate, a polycarbonate, etc.), a metal film, another suitable material, or combinations thereof. As such, the fluid impermeable barrier 102 substantially prevents the fluids from exiting the portions of the chamber 104 that are spaced from the opening 106. In an embodiment, the fluid impermeable barrier 102 can be air permeable and fluid impermeable. In such an embodiment, the fluid impermeable barrier 102 can be formed of a hydrophobic material that defines a plurality of pores. In an example, the one or more portions of the outer surface of the fluid impermeable barrier 102 can be formed from a soft and/or smooth material thereby reducing chaffing.

The fluid collection device 100 can include a fluid permeable membrane 118 disposed in the chamber 104. The fluid permeable membrane 118 can cover at least a portion (e.g., all) of the opening 106. The fluid permeable membrane 118 can be configured to wick any fluid away from the opening 106 thereby preventing the fluid from escaping the chamber 104. The fluid permeable membrane 118 can also wick the fluid generally towards an interior of the chamber 104, as will be discussed in more detail below. The fluid permeable membrane 118 can include any material that can wick the fluid. For example, the fluid permeable membrane 118 can include fabric, such as a gauze (e.g., a silk, linen, or cotton gauze), another soft fabric, or another smooth fabric. The permeable properties referred to herein can have wicking, capillary action, diffusion, or other similar properties or processes, and are referred to herein as "permeable" and/or "wicking." Such "wicking" may not include absorption into the permeable material. Forming the fluid permeable membrane 118 from gauze, soft fabric, and/or smooth fabric can reduce chaffing caused by the fluid collection device 100.

The fluid collection device 100 can include a fluid permeable support 120 disposed in the chamber 104. The fluid permeable support 120 is configured to support the fluid permeable membrane 118 since the fluid permeable membrane 118 can be formed from a foldable, flimsy, or otherwise easily deformable material. For example, the fluid permeable support 120 can be positioned such that the fluid permeable membrane 118 is disposed between the fluid permeable support 120 and the fluid impermeable barrier 102. As such, the fluid permeable support 120 can support and maintain the position of the fluid permeable membrane 118. The fluid permeable support 120 can be formed from any fluid permeable material that is less deformable than the fluid permeable membrane 118. For example, the fluid permeable support 120 can include a porous nylon structure. In an embodiment, the fluid permeable support 120 can be omitted from the fluid collection device 100.

In an embodiment, the fluid permeable membrane 118 and the fluid permeable support 120 can at least substantially completely fill the portions of the chamber 104 that are not occupied by the channel 108. In an embodiment, the fluid permeable membrane 118 and the fluid permeable support 120 does not substantially completely fill the portions of the chamber 104 that are not occupied by the channel 108. In such an embodiment, the fluid collection device 100 includes a reservoir 122 disposed in the chamber 104. The reservoir 122 is a substantially unoccupied portion of the chamber 104 defined between the fluid permeable support 120 and the fluid impermeable barrier 102. The fluids that are in the chamber 104 can flow through the fluid permeable membrane 118 and/or fluid permeable support 120 to the reservoir 122. The reservoir 122 can store at least some of the fluids therein.

In an example, the reservoir 122 can be located at the end of the chamber 104 that is closest to the inlet 110. However, the reservoir 122 can be located at different locations in the chamber 104. For example, the reservoir 122 can be located at the end of the chamber 104 that is closest to the outlet 112. In another example, fluid collection device 100 can include multiple reservoirs, such as a first reservoir that is located at the end of the chamber 104 that is closest to the inlet 110 and a second reservoir that is located at the end of the chamber 104 that is closest to the outlet 112. In another example, the fluid permeable support 120 is spaced from at least a portion of the channel 108 and the reservoir 122 can be the space between the fluid permeable support 120 and the channel 108.

Other examples of fluid impermeable barriers, fluid permeable membranes, fluid permeable supports, and chambers are disclosed in U.S. patent application Ser. No. 15/260,103 filed on Sep. 8, 2016, the disclosure of which is incorporated herein, in its entirety, by this reference.

The fluid impermeable barrier 102, the fluid permeable membrane 118 and the fluid permeable support 120 can be configured to have the channel 108 at least partially disposed in the chamber 104. In an example, at least one of the fluid permeable membrane 118 and the fluid permeable support 120 can be configured to form a space that accommodates the channel 108. In an example, the fluid impermeable barrier 102 can define a first aperture 124 and a second aperture 126. The first and second apertures 124, 126 can be sized to have the channel 108 extend therethrough or at least one tube (not shown) extend therethrough. The at least one tube can be configured to be coupled to the inlet 110 and/or the outlet 112 when the inlet 110 or the outlet 112 is disposed in the chamber 104. The first and second apertures 124, 126 can be configured to form an at least substantially fluid tight seal against the channel 108 or the at least one tube thereby substantially preventing the fluids from escaping the chamber 104.

As previously discussed, the channel 108 is configured to be coupled to and at least partially extend between a gas source and a fluid storage container. In an example, the channel 108 is configured to be directly connected to at least one of the gas source or the fluid storage container. In such an example, the channel 108 can extend from the fluid impermeable barrier 102 by at least one foot, at least two feet, at least three feet, or at least six feet. In an example, the channel 108 is configured to be indirectly connected to at least one of the gas source or the fluid storage container with at least one tube that is distinct and separate from the channel 108. In some embodiments, a portion of the channel 108 and/or tuber connected to the channel 108 is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are configured to connect (e.g., directly or indirectly) to the gas source and the fluid storage container. In an example, the inlet 110 and/or the outlet 112 can form a male connector. In another example, the inlet 110 and/or the outlet 112 can form a female connector. In an example, the inlet 110 and/or the outlet 112 can include ribs that are configured to facilitate secure couplings. In an example, the inlet 110 and/or the outlet 112 can form a tapered shape. In some examples, the channel 108 may include one or more portions that are resilient, such as to by having one or more of a diameter or wall thickness that allows the channel 108 to be flexible. In an example, the inlet 110 and/or the outlet 112 can include a rigid or flexible material.

As previously discussed, the channel 108 includes at least one aperture 114. In an embodiment, the at least one aperture 114 includes a single aperture 114. In such an embodiment, the aperture 114 can be located at or near a gravimetrically low point of the chamber 104. For example, as illustrated, the single aperture 114 is disposed in or adjacent to the at least one reservoir 122, at or near the inlet 110, or at or near the outlet 112. Locating the single aperture 114 at or near a gravimetrically low point of the chamber 104 enables the single aperture 114 to receive more of the fluids than if the single aperture 114 was located elsewhere and reduce the likelihood of pooling (e.g., pooling of the fluids can cause microbe growth and foul odors). For instance, the fluids in the fluid permeable membrane 118 and the fluid permeable support 120 can flow in any direction due to capillary forces. However, the fluids may exhibit a preference to flow in the direction of gravity, especially when at least a portion of the fluid permeable membrane 118 and/or the fluid permeable support 120 is saturated with the fluids.

Figure 3:
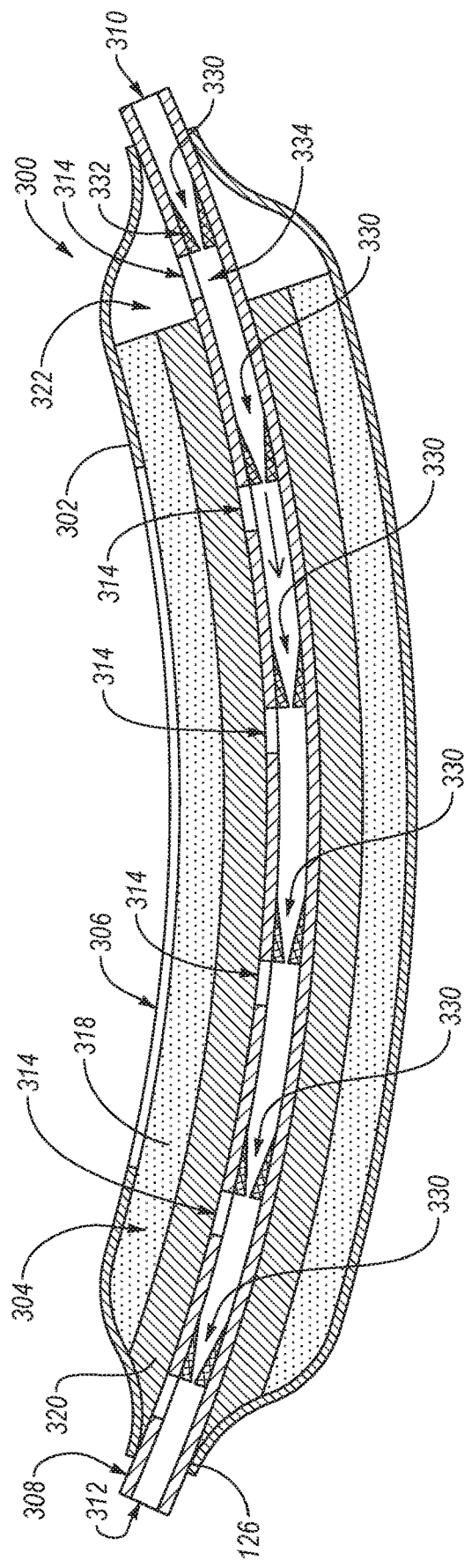
FIG. 3 is a schematic cross-sectional view of a fluid collection device that includes a channel having a plurality of apertures and/or suction devices, according to an embodiment.

In an example, the at least one aperture 114 includes a plurality of apertures 114 (see FIG. 3). In such an example, at least one of the plurality of apertures 114 is located at or near a gravimetrically low point for substantially the same reasons as the single aperture 114 discussed above. In an example, at least one of the remaining apertures 114 can be also located at or near the gravimetrically low point of the chamber 104 thereby increasing the rate at which the fluids can be removed therefrom. In another example, at least one of the remaining apertures 114 can be spaced from the gravimetrically low point of the chamber 104, such as adjacent to portions of the fluid permeable membrane 118 or the fluid permeable support 120. In such an instance, the aperture(s) 114 that are adjacent to the fluid permeable membrane 118 or the fluid permeable support 120 can receive fluids directly from the fluid permeable membrane 118 or the fluid permeable support 120, thereby reducing stagnation of the fluids (e.g., stagnation of the fluids can cause microbe growth and foul odors).

Gas from the gas source is configured to flow from the inlet 110 to the outlet 112 of the channel 108 (as show with an arrow). The flow of the gas through the channel 108 causes any fluid that enters the channel 108 to flow towards the outlet 112. The aperture 114 can be configured to limit the amount of the gas that flows therethrough. For example, the aperture 114 can extend through one or more walls 128 at an acute angle relative to the flow of the gas or can include a check valve.

In an example, the channel 108 is configured to be at least insertable into the chamber 104. In such an example, the channel 108 can include one or more markers (not shown) on an exterior thereof that are configure to facilitate insertion of the channel 108 into the chamber 104. For example, the channel 108 can include one or more markings thereon that are configured to prevent over or under insertion of the channel 108, such as when the channel 108 defines a aperture 114 that is configured to be disposed in or adjacent to the reservoir 122. In another example, the channel 108 can include one or more markings thereon that are configured to facilitate correct rotation of the channel 108 relative to the chamber 104. In an example, the one or more markings can include a line, a dot, a sticker, or any other suitable marking. Further, the fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In some examples, the markings may include one or more of alignment guide or an orientation indicator, such as a stripe or hashes. Such markings may be positioned to align the device 100 to one or more anatomical features such as a pubic bone, etc.

In an example, one or more components of the fluid collection device 100 can include an antimicrobial material, such as an antibacterial material on any surface of the fluid collection device that may contact the wearer or the bodily fluid of the wearer. The antimicrobial material can include an antimicrobial coating, such as a nitrofurazone or silver coating. The antimicrobial material can inhibit microbial growth, such as microbial growth due to pooling or stagnation of the bodily fluids. In some examples, one or more components (e.g., impermeable barrier 102, channel 108, etc.) of the fluid collection device 100 can include an odor blocking or absorbing material such as a cyclodextrine containing material or a thermoplastic elastomer (TPE) polymer.

Figure 2:
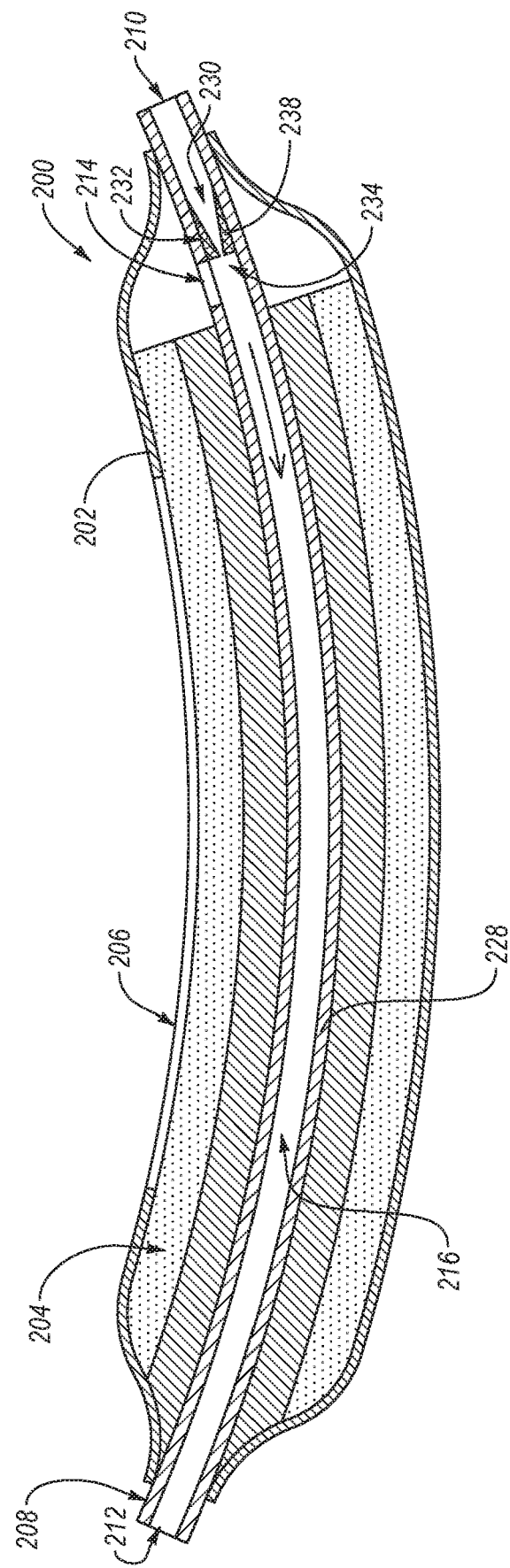
FIG. 2 is a schematic cross-sectional view of a fluid collection device that is configured to actively pull the fluids into a channel thereof, according to an embodiment.

The fluid collection device 100 of FIG. 1 does not use suction to pull fluids into the channel 108. Instead, the fluid collection device 100 relies on gravity, capillary reaction, etc. to pull the fluids into the channel 108. However, the fluid collection devices disclosed herein can configured to use suction to pull the fluids into the channels thereof. FIG. 2 is a schematic cross-sectional view of a fluid collection device 200 that is configured to actively pull the fluids into a channel 208 thereof, according to an embodiment. Except as otherwise disclosed herein, the fluid collection device 200 is the same or substantially similar to any of the fluid collection devices disclosed herein. For example, the fluid collection device 200 can include a fluid impermeable barrier 202 that at least partially defines a chamber 204 and an opening 206. The fluid collection device 200 can also include a fluid permeable membrane 118 and a fluid permeable support 120 disposed in the chamber 204. The fluid collection device 200 can further include a channel 208 that is at least partially disposed in the chamber 204.

The channel 208 includes a suction device 230 (e.g., Venturi suction device) that is configured to generate a suction force when a gas flows through the channel 208. The suction device 230 can include a narrowed section 232 positioned upstream from an expanded section 234. In the narrowed section 232, the diameter of the interior 216 of the channel 208 generally decreases along the flow path of a gas (shown with an arrow) in the channel 208. In an example, the narrowed section 232 can be formed by placing at least one obstacle 238 in the channel 208 that are integrally formed with or distinct from the walls 228 of the channel 208, increasing a thickness of the walls 228 of the channel 208, or using any other suitable method. The diameter of the interior 216 of the channel 208 in the narrowed section 232 continues to decrease along the flow path until the diameter exhibits a minimum diameter. The expanded section 234 of the suction device 230 is downstream from the narrowed section 232. The diameter of the interior 216 of the channel 208 in the expanded section 234 increases along the flow path. In an example, as illustrated, the diameter of the interior 216 of the channel 208 can suddenly increase. In another example, the diameter of the interior 216 of the channel 208 can gradually increase. In either example, a vacuum is created at or slightly downstream from the minimum diameter.

The channel 208 includes at least one aperture 214 that is positioned adjacent to the vacuum that is created by the suction device 230. For example, the aperture 214 can be located adjacent to on the downstream side of the minimum diameter of the narrowed section 232 or proximate to and downstream from the narrowed section 232. The vacuum generated by the suction device 230 creates a suction force in the chamber 204. The suction force can pull more of the fluids that are present into the chamber 204 into the channel 208 thereby reducing pooling or stagnation of the fluids in the chamber 204.

As previously discussed, the channels of the fluid collection devices disclosed herein can include a plurality of apertures. Additionally, the channels can also include a plurality of suction devices that correspond to at least some of the plurality of apertures. FIG. 3 is a schematic cross-sectional view of a fluid collection device 300 that includes a channel 308 having a plurality of apertures 314 and/or suction devices 330, according to an embodiment. Except as otherwise disclosed herein, the fluid collection device 300 can be the same as or similar to any of the fluid collection devices disclosed herein. For example, the fluid collection device 300 can include a fluid impermeable barrier 302 that defines a chamber 304 and an opening 306. The fluid collection device 300 can also include a fluid permeable membrane 318 and a fluid permeable support 320 disposed in the chamber 304. The channel 308 can also be at least partially disposed in the chamber 304.

The channel 308 includes a plurality of apertures 314 formed therein. In an example, at least one of the plurality of apertures 314 is located at or near a gravimetrically low point of the chamber 304, such as disposed in or adjacent to a reservoir 322. The remainder of apertures 314 can also be located at, near, and/or spaced from the gravimetrically low point of the chamber 304.

The channel 308 can also include a plurality of suction devices 330. The suction devices 330 can be the same or similar to the suction device 230 of FIG. 2. For example, each of the suction devices 330 can include a narrowed section 332 having a minimum diameter and an expanded section 334. The suction devices 330 can be disposed in the channel 308 such that at least some (e.g., all) of the apertures 314 are positioned adjacent or proximate to and downstream from the minimum diameter of a corresponding suction device 330. The plurality of suction devices 330 can create a suction force that pulls the fluids into the channel 308 from a variety of locations in the chamber 304. For example, the plurality of suction devices 330 can create suction forces that pulls fluids from a variety of locations in the chamber 304 thereby limiting pooling or stagnation in the chamber 304 compared to a substantially similar channel that one suction device or no suction device.

Figure 4:
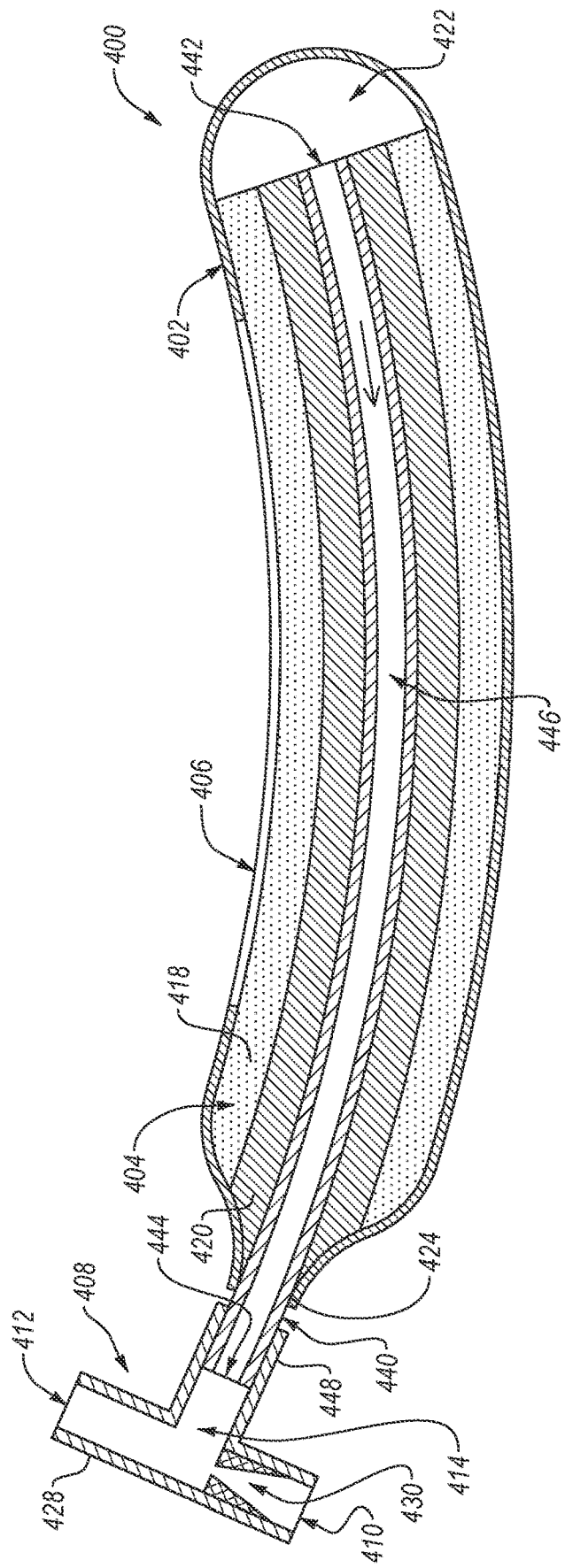
FIG. 4 is a schematic cross-sectional view of a fluid collection device that includes a channel that is spaced from the chamber of the fluid collection device, according to an embodiment.

FIGS. 1-3 illustrate and describe fluid collection devices that include channels that are at least partially disposed in the chambers thereof. However, in some embodiments, the channel can be spaced from the chamber of the fluid collection device. FIG. 4 is a schematic cross-sectional view of a fluid collection device 400 that includes a channel 408 that is spaced from the chamber 404 of the fluid collection device 400, according to an embodiment. Except as otherwise disclosed herein, the fluid collection device 400 can be the same as or substantially similar to any of the fluid collection devices disclosed herein. For example, the fluid collection device 400 can include a fluid impermeable barrier 402 that defines a chamber 404 and an opening 406. The fluid collection device 400 can also include at least one of a fluid permeable membrane 418, a fluid permeable support 420, and a reservoir 422 disposed in the chamber 404.

The fluid collection device 400 includes a conduit 440 that is at least partially disposed in the chamber 404. The conduit 440 defines at least one entrance 442 (e.g., a plurality of entrances) and an exit 444. The entrance 442 enable at least some of the fluids that are present in the chamber 404 to enter an interior 446 of the conduit 440. In an example, the conduit 440 can be configured to have the at least one entrance 442 located at, near, or spaced a gravimetrically low point of the chamber 404. In an example, the conduit 440 can be configured to have the at least one entrance 442 disposed in or adjacent to the reservoir 422.

The conduit 440 can be configured to allow the channel 408 to be in fluid communication with the chamber 404. In other words, the channel 408 is in indirect fluid communication with the chamber 404 via the conduit 440. As such, the fluid impermeable barrier 402 can define an aperture 424. In an example, as illustrated, the aperture 424 enables the conduit 440 to extend outwardly from the chamber 404 when the conduit 440 is only partially disposed in the chamber 404. In another example, the aperture 424 enables a tube to extend into the chamber 404 and be attached to the conduit 440 when the conduit 440 is completely disposed in the chamber 404. For example, the conduit 440 may extend into the fluid impermeable barrier 402 from the first end region (e.g., proximate to the aperture 424) and may extend to the second end region (e.g., opposite the first end region) to a point proximate to the reservoir 422 such that the at least one entrance 442 is in fluid communication with the reservoir 422. In some embodiments (not shown), the conduit 440 may enter the second end region and the at least one entrance 442 of the conduit 440 may be disposed in the second end region (e.g., in the reservoir 422).

The channel 408 can include one or more walls 428 that define an inlet 410 and an outlet 412. The inlet 410 can be configured to be coupled to a gas source (not shown) and the outlet 412 can be configured to be coupled to a fluid storage container (not shown) such that gas flows through the channel 408 in the direction shown with an arrow. The channel 408 also includes a passageway 414 that is configured to be in fluid communication, either directly (as shown) or indirectly (via at least one tube), with the conduit 440. In an example, the channel 408 can include one or more passageway walls 448 that defines the passageway 414. The one or more passageway walls 448 can extend outwardly from the wall 428 such that the walls 428 and the passageway walls 448 can collectively form a generally T-shape. In an example, the channel 408 also includes a suction device 430. The suction device 430 can provide a suction force that pulls fluid into the conduit 440. In an example, the suction device 430 can be omitted from the channel 408.

As previously discussed, the channel 408 can be configured to be in fluid communication with the conduit 440. In an example, as illustrated, the channel 408 and the conduit 440 are distinct from each other. In such an example, the channel 408 and the conduit 440 can be attached together each using any suitable method. For instance, the passageway 414 of the channel 408 can form a female connector and the exit 444 of the conduit 440 can form a male connector that is configured to be coupled to the passageway 414. In another instance, the passageway 414 can form a male connector and the exit 444 can form a female connector that is configured to be coupled to the passageway 414. In another instance, the passageway 414 can include a male or female connector, the exit 444 can include a male of female connector, and the fluid collection device 400 can include at least one tube (not shown) that is attached to and extends between the passageway 414 and the exit 444. In another example, the channel 408 and the conduit 440 can be integrally formed together (e.g., exhibit single piece construction).

Figure 5A:
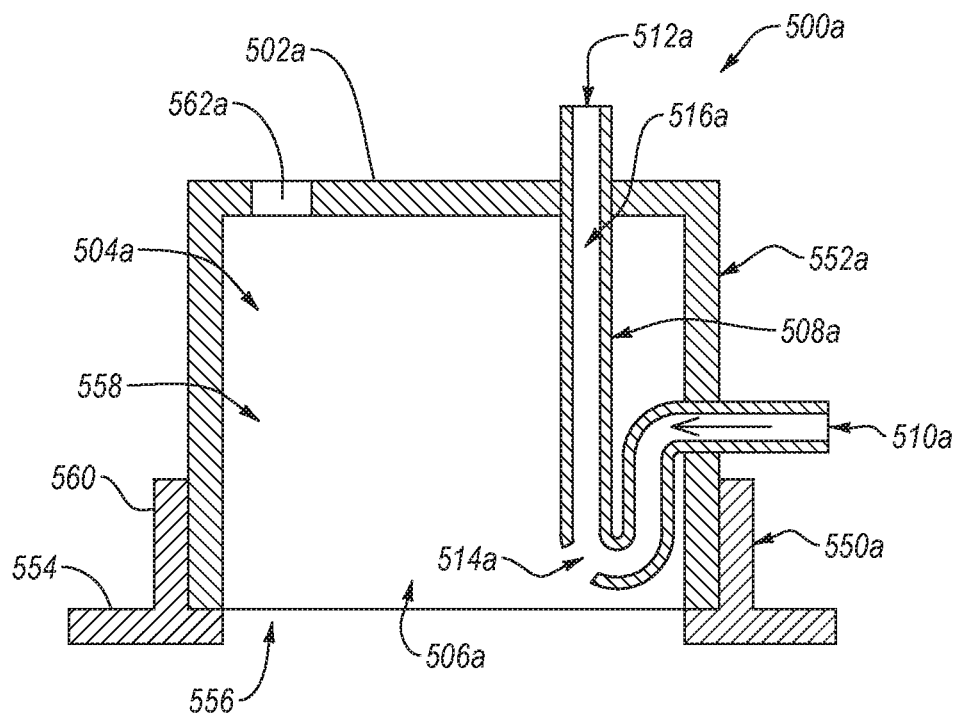
FIGS. 5A-5C are schematic cross-sectional views of male fluid collection devices, according to an embodiment.
Figure 5B:
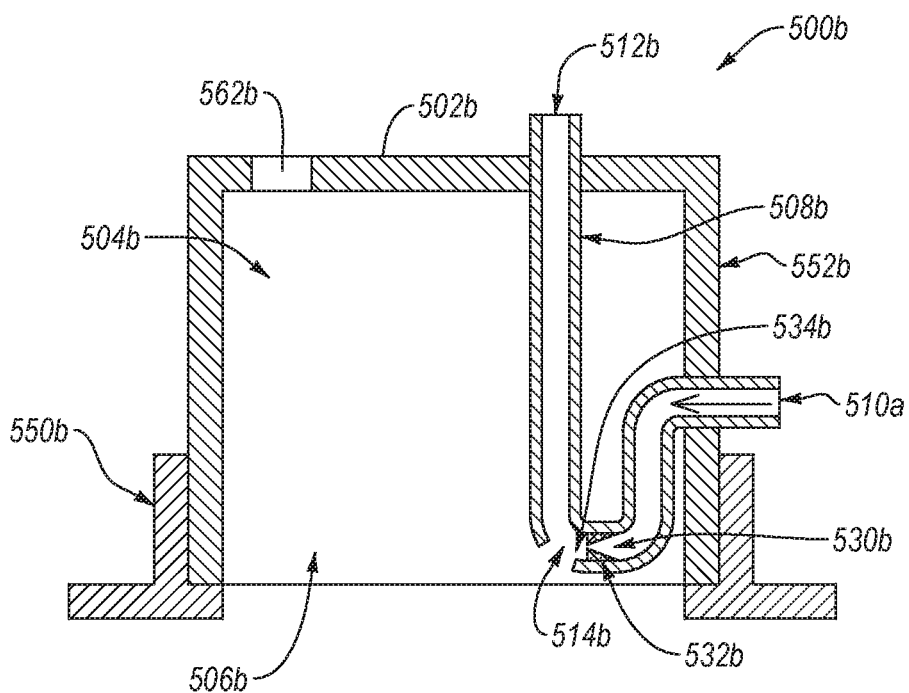
Figure 5C:
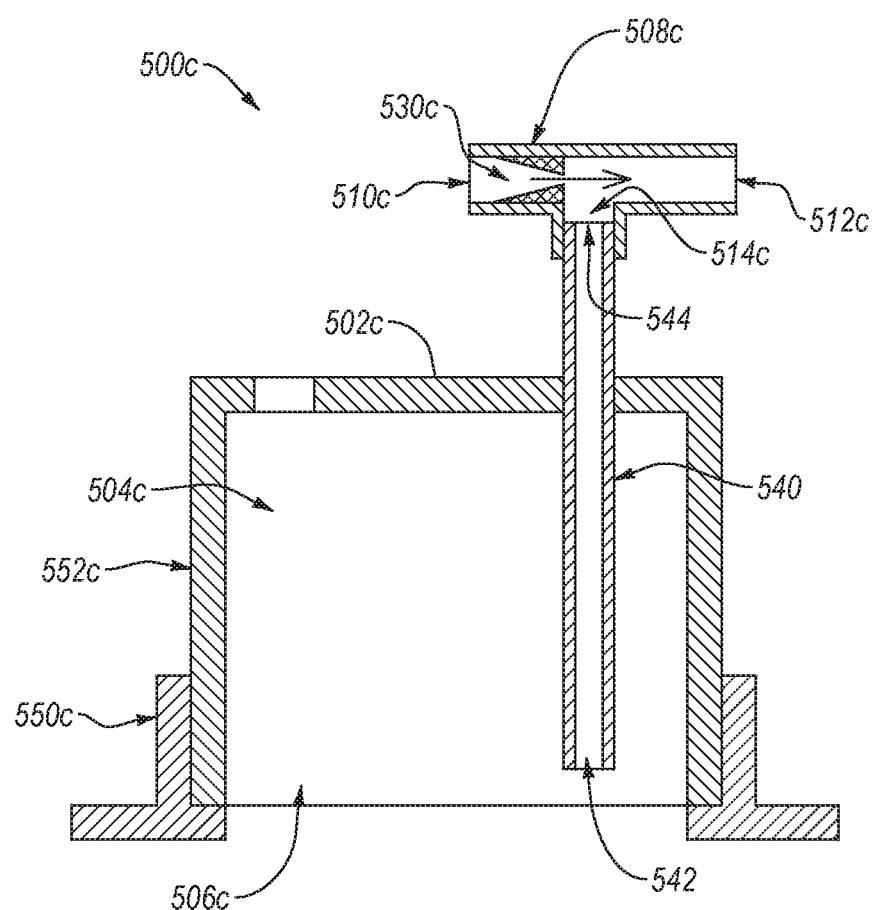

The fluid collection devices shown in FIGS. 1-4 are examples of female fluid collection devices that are configured to collect fluids from females (e.g., collect urine from a female urethra). However, the any of the fluid collection devices disclose herein can be configured configure to collect fluids from males (e.g., collect urine from a male urethra). FIGS. 5A to 5C are schematic cross-sectional views of male fluid collection devices 500a-c, according to different embodiments.

Referring to FIG. 5A, the fluid collection device 500a includes a receptacle 550a and a cup portion 552a. The receptacle 550a is configured to be coupled to skin that surrounds the male urethra and have the male urethra positioned therethrough. For example, the receptacle 550a can include an annular base 554 that defines a hole 556. The annular base 554 is configured to be positioned around the male urethra (e.g., positioned around the penis) and the hole 556 can be configured to have the male urethra positioned therethrough. The annular base 554 can also be configured to be coupled (e.g., adhesively attached, such as with a hydrogel adhesive) to the skin around the male urethra. In an example, the annular base 554 can exhibit the general shape of the skin surface that the annular base 554 is configured to be coupled and/or can be flexible thereby allowing the annular base 554 to conform to the shape of the skin surface. The receptacle 550a also defines a hollowed region 558 that is configured to have the cup portion 552a disposed therein. For example, the receptacle 550a can include a flange 560 that extends upwardly from the annular base 554 that partially defines the hollowed region 558. The hollowed region 558 is deep enough that the cup portion 552a is unlikely to be accidentally removed from the hollowed region 558 (e.g., the hollowed region 558 is at least 1 cm deep, at least 2 cm deep, or at least 5 cm deep).

The cup portion 552a includes a fluid impermeable barrier 502a that is sized and shaped to fit into the hollowed region 558 of the receptacle 550a. The fluid impermeable barrier 502a partially defines a chamber 504a. The fluid impermeable barrier 502a also defines an opening 506a extending through the fluid impermeable barrier 502a that is configured to have a male urethra positioned therethrough. The fluid impermeable barrier 502a can also define at least one hole 562a that allows the chamber 504a to remain substantially at atmospheric pressure. The cup portion 552a also include a channel 508a that is at least partially disposed in the chamber 504a. The channel 508a includes an inlet 510a that is configured to be communicably coupled to an gas source (not shown) and an outlet 512a that is configured to be communicably coupled to a fluid storage container (not shown) such that a gas flows through the channel 508a in the direction show by the arrow. The channel 508a also defines at least one aperture 514a that allows an interior 516a of the channel 508a to be in fluid communication with the chamber 504a. For example, at least the aperture 514a is disposed in the chamber 504a.

In an example, the chamber 504a can be substantially empty due to the varying sizes and rigidity of the male penis. However, the outermost regions of the chamber 504a can include a porous material (e.g., that is the same or similar to the fluid permeable membranes and/or fluid permeable supports disclosed herein) configured to blunt a stream of urine from the male urethra thereby limiting splashing and/or to direct the fluids to a selected region of the chamber 504a. Since the chamber 504a is substantially empty (e.g., substantially all of the chamber 504a forms a reservoir), the fluids are likely to pool at a gravimetrically low point of the chamber 504a. The gravimetrically low point of the chamber 504 can be at an intersection of the skin of an individual and the fluid collection device 500a, a corner formed in the cup portion 552a, or another suitable location. The aperture 514a of the channel 508a can be configured and positioned to be adjacent or proximate to the gravimetrically low point of the chamber 504a. In an example, the chamber 504 may include at least one of a fluid permeable membrane (not shown) or support (not shown) disposed therein that are similar to the fluid permeable membranes and supports, respectively, disclosed herein.

During operation, a male using the fluid collection device 500a can discharge fluids (e.g., urine) into the chamber 504a. The fluids can pool or otherwise be collected in the chamber 504a. At least some of the fluids can enter the interior 516a of the channel 508a via the aperture 514a. The flow of gas from the inlet 510a to the outlet 512a can push the fluids that enter the channel 508a towards the outlet 512a. During operation, the hole 562a substantially maintains the pressure in the chamber 504a at atmospheric pressure even though fluid is introduced into and subsequently removed from the chamber 504a, gas can be introduced into and/or removed from the chamber 504a via the channel 508a, etc.

FIG. 5B illustrates a fluid collection device 500b that, except as otherwise disclosed herein, is the same as or substantially similar to the fluid collection device 500a of FIG. 5A. For example, the fluid collection device 500b can include a receptacle 550b and a cup portion 552b. The cup portion 552b can include a fluid impermeable barrier 502b that defines a chamber 504b and an opening 506b. The cup portion 552b can also include a channel 508b that is at least partially disposed in the chamber 504b. For example, the channel 508b defines an inlet 510b, an outlet 512b, and at least one aperture 514b.

The channel 508b also includes at least one suction device 530b disposed therein. The suction device 530b can be the same as or substantially similar to the suction devices 230, 330, or 430 of FIGS. 2-4. For example, the suction device 530b includes a narrowed section 532b having a minimum diameter and an expanded section 534b that is downstream from the narrowed section 532b. The suction device 530b can be positioned such that the aperture 514b is adjacent to the minimum diameter thereof or proximate to and downstream from the narrowed section 532b. The suction device 530b can apply a suction force that causes more of the fluid to enter the channel 508b thereby limiting pooling or stagnation in the chamber 504b. The hole 562b substantially maintains atmospheric pressure in the chamber 504b thereby reducing discomfort and rupturing of capillaries that can be caused by the suction force.

FIG. 5C illustrates a fluid collection device 500c that, except as otherwise disclosed herein, is the same as or substantially similar to the fluid collection devices 500a, 500b of FIGS. 5A and 5B. For example, the fluid collection device 500c can include a receptacle 550c and a cup portion 552c. The cup portion 552c can include a fluid impermeable barrier 502c that defines a chamber 504c and an opening 506c.

The fluid collection device 500c also includes a channel 508c that is spaced from the chamber 504c. The channel 508c can be the same as or substantially similar to the channel 408 of FIG. 4. For example, the channel 508c can define an inlet 510c, an outlet 512c, and at least one passageway 514c. The channel 508c can also include a suction device 530c.

The fluid collection device 500c also includes a conduit 540 that is at least partially disposed in the chamber 504c. The conduit 540 is configured to allow the channel 508c to be in indirect fluid communication with the chamber 504c. The conduit 540 include at least one entrance 542 and an exit 544 downstream from the entrance 542. The conduit 540 can be attached to the channel 508c using any of the techniques disclosed herein.

As previously discussed, the fluid collection devices can form part of a system that includes a gas source and a fluid storage container. FIG. 6A is a schematic of a fluid collection system 664a, according to an embodiment. The system 664a includes a fluid collection device 600a that includes a channel (not shown) at least partially disposed in the chamber of the fluid collection device 600a, such as any of the fluid collection devices 100, 200, 300, 500a, 500b of FIG. 1-3, 5A, or 5B. The system 664a also include a gas source 668a that is positioned upstream from the fluid collection device 600a and is in fluid communication with the inlet of a channel of the fluid collection device 600a. For example, the gas source 668a can be in direct fluid communication with the inlet (e.g., directly attached to the inlet) or can be in indirect fluid communication with the inlet via at least one first tube 670a. The gas source 668a can include any suitable gas source, such as a compressed tank of gas (e.g., atmospheric air, oxygen, nitrogen, etc.), a pump, a compressor, or a wall gas source. The system 664b also includes a fluid storage container 672a that is positioned downstream from the fluid collection device 600a and is in fluid communication with an outlet of the channel. For example, the fluid storage container 672a can be in directly fluid communication with the outlet (e.g., directly attached to the outlet) or can be in indirect fluid communication with the outlet via at least one second tube 674a. The fluid storage container 672a can include any suitable container that can store fluids, such as a container having a container inlet and an air vent.

In an example, the first tube 670a, the second 674a, or the channel of the fluid collection device 600a can include a flow meter (not shown) that is configured to measure the flow of the gas and/or fluids therein. In another example, the system 664a can include a securement device (e.g., a STAT-LOCK® securement device, not shown) that is configured to secure the first tube 670a, the second 674a, or the channel of the fluid collection device 600a to an individual. In an example, the first tube 670a, the second 674a, or the channel of the fluid collection device 600a can be formed from a flexible material, such as from Foley tubes.

In an example, at least one of the second 674a or the channel of the fluid collection device 600a can be formed of an at least partially opaque material which can obscure the fluids that are present therein thereby reducing embarrassment caused by the fluids. For example, least one of the second 674a or the channel of the fluid collection device 600a can be formed from an opaque or nearly opaque material. In another example, least one of the second 674a or the channel of the fluid collection device 600a can be formed from translucent material, such as frosted tubing. Unlike the opaque or nearly opaque material, the translucent material allows a user of the system 664a to notice any issues that are inhibiting the flow of the gas or fluids therethrough.

FIG. 6B is a schematic of a fluid collection system 664b, according to an embodiment. Except as otherwise disclosed herein, the system 664b can be the same as or substantially similar to the system 664a of FIG. 6A. For example, the system 664b can include gas source 668b that is in fluid communication with an inlet of a channel 608 of a fluid collection device 600b (e.g., via at least one first tube 670b) and a fluid storage container 672b that is in fluid communication with an outlet of the channel 608 (e.g., via at least one second tube 674b). However, unlike the system 664a, the channel 608 of the fluid collection device 600b is spaced from a chamber 604 of the fluid collection device 600b. For example, the fluid collection device 600b can be the same or similar to the fluid collection devices 400, 500c of FIG. 4 or 5C. In such an example, the chamber 604 can be in indirect fluid communication with the channel 608 via a conduit 640 or another tube.

Figure 7:
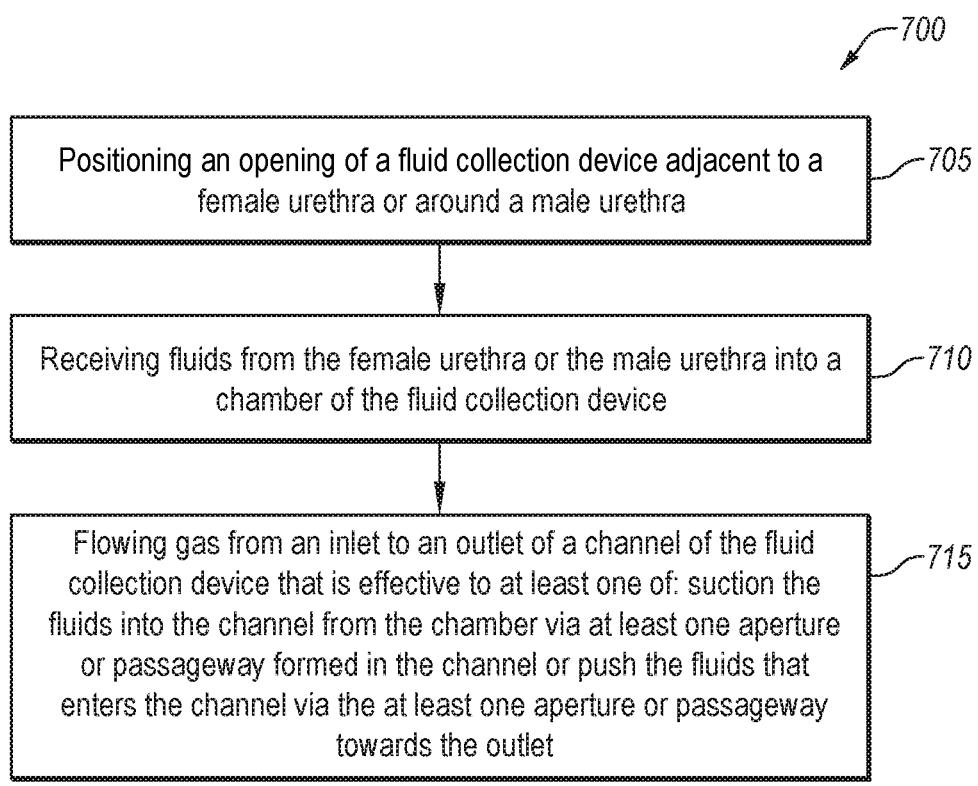
FIG. 7 is a flow diagram of a method to use any of the fluid collection devices and/or fluid collection systems disclosed herein, according to an embodiment.

FIG. 7 is a flow diagram of a method 700 to use any of the fluid collection devices and/or fluid collection systems disclosed herein, according to an embodiment. The method 700 can include act 705, which recites "positioning an opening of a fluid collection device adjacent to a female urethra or around a male urethra." Act 705 may be followed by act 710, which recites "receiving fluids from the female urethra or the male urethra into a chamber of the fluid collection device." Act 710 may be followed by act 715, which recites "flowing gas from an inlet to an outlet of a channel of the fluid collection device that is effective to at least one of: suction the fluids into the channel from the chamber via at least one aperture or passageway formed in the channel or push the fluids that enters the channel via the at least one aperture or passageway towards the outlet."

Acts 705, 710, 715 of the method 700 are for illustrative purposes. For example, the act 705, 710, 715 of the method 700 can be performed in different orders, split into multiple acts, modified, supplemented, or combined. In an example, one or more of the acts 705, 710, 715 of the method 700 can be omitted from the method 700.

Act 705 recites "positioning an opening of a fluid collection device adjacent to a female urethra or around a male urethra." In an example, act 705 can include positioning the opening of a female fluid collection device such that the fluid permeable membrane of the female fluid collection device abuts or is positioned proximate to the female urethra. In another example, act 705 can include positioned a receptacle of a male fluid collection device around the male urethra such that the male urethra is positioned through a hole of the receptacle. In such an example, act 705 can include positioning a cup portion of the male fluid collection device in a hollowed region of the receptacle such that the male urethra is positioned through an opening of the cup portion.

Act 710 recites "receiving fluids from the female urethra or the male urethra into a chamber of the fluid collection device." For example, act 710 can include wicking the fluids away from the opening using a fluid permeable membrane and a fluid permeable support. In another example, act 710 can include receiving the fluids into the chamber of the cup portion of the male fluid collection device. In either example, act 710 can include flowing the fluid towards a portion of the chamber that is in fluid communication, either directly or indirectly, with an aperture (e.g., apertures 114, 214, 314, 514a, or 514b of FIGS. 1-3, 5A, and 5B) or passageway (e.g., passageways 414, 514c of FIGS. 4 and 5C) of a channel. For instance, act 710 can include flowing the fluids to a substantially unoccupied portion of the chamber (e.g., a reservoir), to a gravimetrically low point of the chamber, etc.

Act 715 recites, "flowing gas from an inlet to an outlet of a channel of the fluid collection device that is effective to at least one of: suction the fluids into the channel from the chamber via at least one aperture or passageway formed in the channel or push the fluids that enters the channel via the at least one aperture or passageway towards the outlet." In an example, act 715 can include flowing a gas through a channel that is at least partially disposed in a chamber of the fluid collection device. In another example, act 715 can include flowing gas through a channel that is spaced from the chamber of the fluid collection device. In such an example, act 715 can include flowing a gas through a conduit that is at least partially disposed in the chamber and is in fluid communication with the channel.

In an example, act 715 can include generating a suction force using a suction device. In such an example, act 715 can include flowing gas through and out of at least one narrowed section of a suction device and into an expanded section of the suction device thereby generating a suction force that is effective to suction the fluids into the channel from the chamber. The suction device can be positioned such that the suction force is generated at a aperture or passageway of the channel thereby causing fluids to enter the channel. In an example, act 715 can include generating the suction force using a single suction device or multiple suction devices. In an example, act 715 can include generating the suction force in a channel that is at least partially disposed in the chamber or a channel that is spaced from the chamber.

In an example, the method 700 can include flowing the gas from the gas source towards the fluid storage container. In such an example, the method 700 can include generating the flow of the gas using a pump, allowing the gas to flow out of a compressed tank of gas, providing the gas from a wall gas source, etc. In an example, the method 700 can include collecting the fluids that entered the channel in a fluid storage container that is spaced from the fluid collection device and in fluid communication with the outlet.

While various aspects and embodiments have been disclosed herein, other aspects and embodiments are contemplated. The various aspects and embodiment disclosed herein are for purposes of illustration and are not intended to be limiting.

We claim:

1. A fluid collection device, comprising:
 a fluid impermeable barrier at least partially defining a chamber, the fluid impermeable barrier also defining an opening extending therethrough, the opening configured to be positioned adjacent to a female urethra or have a male urethra positioned therethrough; and
 a single channel that is distinct from the fluid impermeable barrier, the single channel defining and extending between an inlet and an outlet, the outlet positioned downstream from the inlet, the inlet including an inlet connector configured to be in fluid communication with a gas source and the outlet including an outlet connector configured to be in fluid communication with a fluid storage container, the single channel defining at least one aperture or passageway that allows an interior of the single channel to be in fluid communication with the chamber, the at least one aperture or the passageway positioned between the inlet and the outlet;
 wherein the single channel is configured, responsive to flowing gas from the gas source from the inlet to the outlet, to at least one of:
  suction fluids from the chamber into the single channel via the at least one aperture or passageway formed in the single channel; or
  push the fluids that enter the single channel via the at least one aperture or passageway from the chamber towards the outlet.

2. The fluid collection device of claim 1, further comprising:
 a fluid permeable support disposed within the chamber; and
 a fluid permeable membrane disposed on the fluid permeable support, the fluid permeable membrane extending across and covering at least the portion of the opening;
 wherein the opening is configured to be positioned adjacent to the female urethra.

3. The fluid collection device of claim 1, further comprising at least one reservoir disposed in the chamber that is configured to hold a fluid therein, the at least one aperture or passageway of the single channel is disposed in or adjacent to the at least one reservoir.

4. The fluid collection device of claim 3, wherein the reservoir is a substantially unoccupied portion of the chamber, the reservoir located at the end of the chamber.

5. The fluid collection device of claim 1, wherein the single channel is at least partially disposed in the chamber.

6. The fluid collection device of claim 1, wherein the single channel is spaced from the chamber.

7. The fluid collection device of claim 6, further comprising a conduit defining at least one entrance that allows an interior of the single channel to be in fluid communication with the chamber, the conduit extending from the chamber to the at least one aperture or passageway of the single channel.

8. The fluid collection device of claim 1, wherein the single channel includes at least one suction device disposed therein, the suction device includes a narrowed section having a minimum diameter and an expanded section immediately downstream from the minimum diameter;
 wherein the at least one aperture or passageway of the single channel is disposed adjacent or proximate to and downstream from the narrowed section.

9. The fluid collection device of claim 1, wherein the channel defines the aperture disposed in the chamber or the passageway extends parallel to a longitudinal axis of the channel.

10. A fluid collection system, comprising:
 a fluid collection device including:
  a fluid impermeable barrier at least partially defining a chamber, the fluid impermeable barrier also defining an opening extending therethrough, the opening configured to be positioned adjacent to a female urethra or have a male urethra positioned therethrough; and
  a single channel that is distinct from the fluid impermeable barrier, the single channel defining and extending between an inlet and an outlet, the outlet positioned downstream from the inlet, the inlet including an inlet connector configured to be in fluid communication with a gas source and the outlet including an outlet connector configured to be in fluid communication with a fluid storage container, the single channel defining at least one aperture or passageway that allows an interior of the single channel to be in fluid communication with the chamber, the at least one aperture or passageway positioned between the inlet and the outlet;
 the gas source;
 the fluid storage container positioned downstream from the gas source, the fluid storage container configured to hold a fluid;
 wherein the fluid collection device is positioned downstream from the gas source and upstream from the fluid storage container, the inlet in fluid communication with the gas source and the outlet in fluid communication with the fluid storage container;
 wherein the single channel is configured, responsive to flowing a gas from the gas source from the inlet to the outlet, to at least one of:
 suction fluids from the chamber into the single channel via the at least one aperture or passageway formed in the single channel; or
 push the fluids that enter the single channel via the at least one aperture or passageway from the chamber toward the outlet.

11. The system of claim 10, wherein the fluid collection device is in fluid communication with the gas source via at least one first tube and in fluid communication with the fluid collection device via at least one second tube.

12. A method to collect fluid, the method comprising:
 positioning an opening of a fluid collection device adjacent to a female urethra or around a male urethra, the opening defined by a fluid impermeable barrier of the fluid collection device;
 receiving fluids from the female urethra or the male urethra into a chamber of the fluid collection device, the chamber of the fluid collection device at least partially defined by the fluid impermeable barrier; and
 flowing gas from a gas source from an inlet to an outlet of a single channel of the fluid collection device that is effective to at least one of:
 suction the fluids into the single channel from the chamber via at least one aperture or passageway formed in the single channel; or
 push the fluids that enters the single channel via the at least one aperture or passageway towards the outlet;

wherein the channel extending from the inlet to the outlet and the at least one aperture or the passageway are positioned between the inlet and the outlet;

wherein the single channel is distinct from the fluid impermeable barrier, the single channel defining and extending between the inlet and the outlet, the outlet positioned downsream from the inlet, the inlet including an inlet connector in fluid communication with the gas source and the outlet including an outlet connector configured to in fluid communication with a fluid storage container, the single channel defining the at least one aperture or passageway that allows an interior of the single channel to be in fluid communication with the chamber, the at least one aperture or passageway positioned between the inlet and the outlet.

13. The method of claim 12, wherein receiving fluids from the female urethra into the chamber includes:

wicking the fluids away from the opening using a fluid permeable membrane that extends across the opening; and after wicking the fluids away from the opening using the fluid permeable membrane, flowing the fluids through a fluid permeable support disposed within the chamber, the fluid permeable support supporting the fluid permeable membrane.

14. The method of claim 12, wherein receiving fluids from the female urethra or the male urethra into the chamber includes collecting at least some of the fluids in a reservoir of the fluid collection device, wherein the reservoir is in fluid communication to the at least one aperture or passageway of the channel.

15. The method of claim 14, wherein collecting at least some of the fluid in a reservoir includes collecting the fluids in a substantially unoccupied portion of the chamber at an end of the fluid permeable membrane.

16. The method of claim 12, wherein flowing gas from an inlet to an outlet of the channel includes flowing the gas through the channel that is at least partially disposed in the chamber.

17. The method of claim 12, wherein flowing gas from an inlet to an outlet of the channel includes flowing the gas through and out of a narrowed section of the channel, the at least one aperture or passageway is positioned proximate to and downstream from the narrowed section, wherein flowing the gas out of the narrowed section of the channel creates a suction force that is effective to suction the fluids into the channel from the chamber via the at least one aperture or passageway.

18. The method of claim 12, wherein flowing gas from an inlet to an outlet of the fluid collection device includes flowing the gas through and out of a plurality of narrowed sections of the channel, wherein the at least one aperture or passageway of the channel includes a plurality of apertures and a corresponding one of the plurality of apertures is positioned adjacent or proximate to and downstream from each of the plurality of narrowed sections, wherein flowing the gas out of each of the plurality of narrowed sections of the channel creates a suction force that is effective to suction the fluid into the channel from the chamber via the plurality of apertures.

19. The method of claim 12, further comprising, disposing the fluids into the fluid storage container that is spaced from the fluid collection device and in fluid communication with the outlet via at least one tube.

\* \* \* \* \*